(12) United States Patent
Hu et al.

(10) Patent No.: US 11,628,221 B2
(45) Date of Patent: Apr. 18, 2023

(54) PEPTIDE LINKER AND COMBINATION FOR PRODRUGS ACTIVATED BY PROSTATE-SPECIFIC ANTIGEN

(71) Applicant: Rutgers, The State University of New Jersey, New Brunswick, NJ (US)

(72) Inventors: Longqin Hu, Belle Mead, NJ (US); Herve Aloysius, Newburgh, NY (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 17/481,102

(22) Filed: Sep. 21, 2021

(65) Prior Publication Data

US 2022/0088209 A1  Mar. 24, 2022

Related U.S. Application Data

(63) Continuation of application No. 16/482,775, filed as application No. PCT/US2018/016665 on Feb. 2, 2018, now Pat. No. 11,129,901.

(60) Provisional application No. 62/454,244, filed on Feb. 3, 2017.

(51) Int. Cl.
*A61K 47/64* (2017.01)
*A61P 35/00* (2006.01)
*A61K 31/704* (2006.01)
*C07K 7/02* (2006.01)

(52) U.S. Cl.
CPC ............ *A61K 47/64* (2017.08); *A61K 31/704* (2013.01); *A61P 35/00* (2018.01); *C07K 7/02* (2013.01)

(58) Field of Classification Search
None
See application file for complete search history.

(56) References Cited

U.S. PATENT DOCUMENTS 5,147,860 A    9/1992  Kanamaru et al.

OTHER PUBLICATIONS

DeFeo-Jones et al. "A peptide-doxorubicin 'prodrug' activated by prostate-specific antigen selectively kills prostate tumor cells positive for prostate-specific antigen," Nature Medicine, 2000, 6(11), 1248-52 (Year: 2000).*
Aloysius H., Hu L., Improving the Specificity of the Prostate-Specific Antigen Substrate Glutaryl-Hyp-Ala-Ser-Chg-Gln as a Promoiety, Chemical biology & drug design, Oct. 1, 2015; 86(4):837-48.
Barany and Merrifield, The Peptides, 1980, 2:1 284.
Bruno et al., The Deliv., 2013, 4(11):1443-1467.

Defeo-Jones et al, A peptide-doxorubicin 'prodrug' activated by prostate-specific antigen selectively kills prostate tumor cells positive for prostate-specific antigen in vivo, Nature Medicine, 2000, 6, 1248-1252.
Dipaola et al., Characterization of a Novel Prostate-Specific Antigen-Activated Peptide-Doxorubicin Conjugate in Patients With Prostate Cancer, J. Clinical Oncol., 2002, 20:1874-1879.
Dryland and Sheppard, Peptide synthesis. Part 8. A system for solid-phase synthesis under low pressure continuous flow conditions, J. Chem. SoC. Perkin Trans. 1986, I, 125 137.
Ge Y et al., 3-Aminoxypropionat-based linker system for cyclization activation in prodrug design, Bioorganic & medicinal chemistry letters, Feb. 1, 2009, 19(3):941-944.
Geysen et al, Use of peptide synthesis to probe viral antigens for epitopes to a resolution of a single amino acid, Proc. Natl. Acad. Sci., 1984, 81:3998.
Geysen et al., Strategies for epitope analysis using peptide synthesis, J. Immunol. Methods, 1987, 102:259-274.
Hortobagyi et al. Prospective assessment of cardiac toxicity during a randomized phase II trial of doxorubicin and paclitaxel in metastic breast cancer, Semin. Oncol., 1997, 24:S17-65-S17-68.
International Search Report dated Mar. 20, 2018.
Mitchell et al, A new synthetic route to tert-butyloxycarbonylaminoacyl-4-(oxymethyl) phenylacetamidomethyl-resin, an improved support for solid-phase peptide synthesis, J. Org. Chem., 1978, 43:2845-2852.
Nagy A., et al., Schally AV Stability of cytotoxic luteinizing hormone-releasing hormone conjugate (AN-152) containing doxorubicin 14-O-hemiglutarate in mouse and human serum in vitro: implications for the design of preclinical studies. Proceedings of the national Academy of Sciences, Jan. 18, 2000;97(2):829-34. retrieved from the Internet URL: http://www.pnas.org/content/pnas/97/2/829.full.pdf.
Rho et al., Synthesis of New Anthrachcline Derivatives Containing Pyruvic, Aspartic, or N-Acetylaspartic Acid Molecule, Synth. Commun., 2002, 32:1961-1975.
Rho et al., Synthesis of New Anthracycline Derivatives Containing Acetylsalicylic or Palmitic Acid Moiety, Bull. Korean Chem. Soc., 2001, 22:587-592.
Rho et al., Total synthesis of a new 7-deoxyidarubicinone derivative through the functionalization of an A-ring side chain, Bull. Korean Chem. Soc., 2000, 21:774-778.
Weiss, RB, The anthracyclines: will we ever find a better doxorubicin?, Semin. Oncol., 1992 19:670-686.
Wong et al., PSA-specific and non-PSA-specific conversion of a PSA-targeted peptide conjugate of doxorubicin to its active metabolites. Drug Metab. Dispos., 2001, 29:313-318.
Written Opinion dated Mar. 20, 2018.

(Continued)

*Primary Examiner* — Christina Bradley
(74) *Attorney, Agent, or Firm* — Gorman IP Law, APC

(57) ABSTRACT

The present disclosure is directed to a series of target-selective chemotherapeutic ester prodrugs comprising PSA-cleavable peptides that promote the delivery of free doxorubicin and other chemotherapeutic agents into the prostate and/or prostate tumors with greater efficiency.

18 Claims, 14 Drawing Sheets

Specification includes a Sequence Listing.

(56) References Cited

OTHER PUBLICATIONS

Xu X., et al., Molecular Pharmacology of the Interaction of Anthracyclines with Iron, Molecular Pharmacology Aug. 2005, 68 (2) 261-271; DOI: https://doi.org/10.1124/mol.105.013383.
Yang YH et al., Enzyme-mediated hydrolytic activation of prodrugs, Acat Pharmaceutica Sinica B., Oct. 1, 2011; 1(3):143-59 Retrieved from the Internet. URL: https://ac.els-cdn.com/S2211383511000645/1-s2.0-S2211383511000645-main.pdf? tid=af976090-bd03-4c51-bf21-ab68b1f63d4e&acdnat=1520438807_c66ba7af76274dff8fb70446D4920ce.

* cited by examiner

FIG. 11

| Compound | Structure | MS (M + H)+ |
|---|---|---|
| 4 | 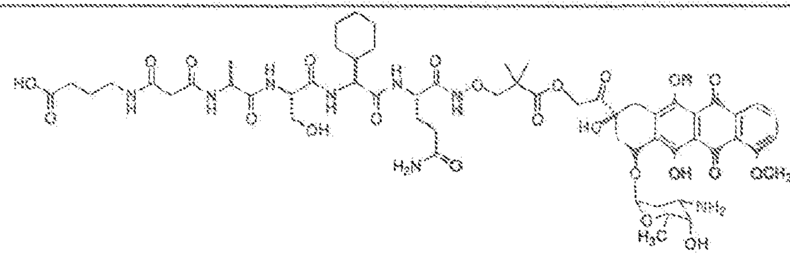 | 1255.53 |
| 5 | 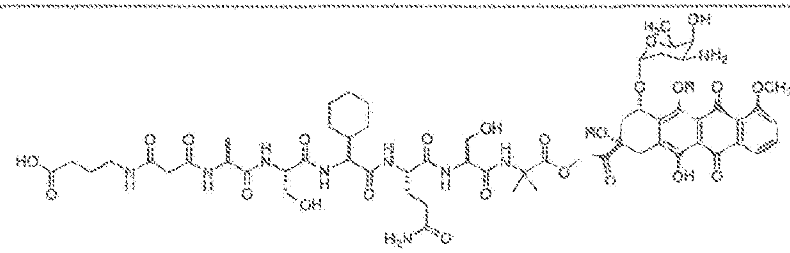 | 1312.55 |
| 6 | 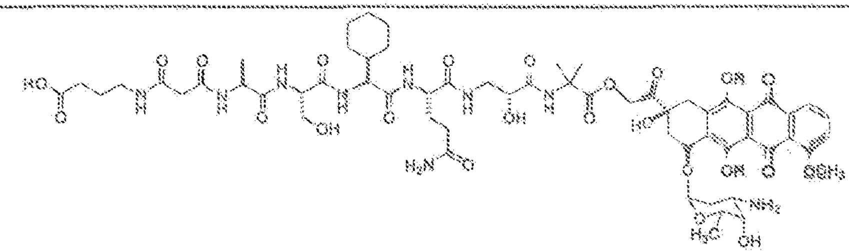 | 1312.55 |

PEPTIDE LINKER AND COMBINATION FOR PRODRUGS ACTIVATED BY PROSTATE-SPECIFIC ANTIGEN

I. CROSS REFERENCE

This Nonprovisional application is a Continuation application of application Ser. No. 16/482,775 which was filed on Aug. 1, 2019, which is the National Phase Application Under 35 U.S.C. § 371 of PCT International Application No. PCT/US2018/016665 filed on Feb. 2, 2018, which claims priority under 35 U.S.C. § 119 on Patent Application No. 62/454,244 filed in the United States on Feb. 3, 2017, the entire contents of each of which are hereby incorporated by reference.

II. STATEMENT REGARDING THE SEQUENCE LISTING

The Sequence Listing associated with this application is provided in text format in lieu of a paper copy and is hereby incorporated by reference into the Specification. The name of the text file containing the Sequence Listing is 2018-02-02-7051-0101PWO1_ST25.txt. The text file is about 5 KB, was created on Feb. 2, 2018, and is being submitted electronically via EFS-Web.

III. BACKGROUND

Doxorubicin (Dox) is highly effective against a wide spectrum of solid tumors but causes dose-dependent cardiomyopathy (Hortobagyi et al. (1997) *Semin. Oncol.* 24:S17-65-S17-68; Weiss (1992) *Semin. Oncol.* 19:670-686; Xu et al. (2005) *Mol. Pharmacol.* 68:261-271). Feasibility of targeted delivery of doxorubicin (and other cytotoxic agents) to prostate cancer cells via selective activation of peptide-linked prodrugs by prostate-specific antigen (PSA) has been demonstrated for several prodrugs, such as, for example, L-377,202 (Glutaryl-Ser-Ala-Ser-Chg-Gln-Ser-Leu-Dox) (SEQ ID NO: 1) (DeFeo-Jones et al. (2000) *Nat. Med.* 6:1248-1252). However, one general caveat with this approach is reliance on endogenous aminopeptidases to convert intermediate peptide- or amino-acid-drug conjugates into the cytotoxic agent following PSA-mediated hydrolysis of the prodrug. For example, Ser-Leu-Doxorubicin, which is generated through PSA-mediated hydrolysis of the Gln-Ser bond of L-377,202, must subsequently be converted to doxorubicin by putative endogenous aminopeptidases through multiple enzymatic steps.

Although significant amounts of Leu-Doxorubicin were formed in vivo in preclinical species and humans, this conjugate is 10-fold less cytotoxic (Wong et al. (2001) *Drug Metab. Dispos.* 29:313-318) and is not anticipated to produce the same cell killing effects as doxorubicin in prostate tumors. In addition, Leu-Doxorubicin is an active metabolite found to circulate in plasma along with doxorubicin at levels high enough to raise safety concerns (DiPaola et al. (2002) *J. Clin. Oncol.* 20:1874-1879). In order to maintain or improve the tumor selectivity of PSA-targeted prodrugs, direct and efficient delivery of free drug into the tumor microenvironment of the prostate must be achieved.

Direct and efficient delivery of free doxorubicin (and anthracyclines with similar structural features) into the microenvironment of prostate tumors can be promoted by coupling PSA-cleavable peptides to a readily accessible hydroxyl functional group, such as the C-14 α-hydroxyl of doxorubicin. This selective delivery of free doxorubicin into PSA-secreting tumor cells, without the assistance of proteases other than PSA, has not previously been demonstrated.

In the case of L-377,202, the PSA-cleavable peptide is coupled to the aminoglycoside of doxorubicin; unlike amide linkages to the aminoglycoside group, introduction of an ester bond between the PSA-cleavable peptide and the drug presents opportunities for non-enzymatic cyclization and subsequent release of free doxorubicin following PSA hydrolysis. Furthermore, improved peptide prodrugs that selectively deliver free doxorubicin into prostate tumors may reduce significant side effects caused by circulating active metabolites. Such prodrugs must also be capable of rapid cleavage by PSA for treatment of prostate cancer and be useful for targeted drug delivery in other prostate diseases such as prostatitis and benign prostatic hyperplasia (BPH).

IV. SUMMARY OF THE INVENTION

The present disclosure is directed to a series of target-selective chemotherapeutic ester prodrugs comprising PSA-cleavable peptides that promote the delivery of free doxorubicin and other chemotherapeutic agents into the prostate and/or prostate tumors with greater efficiency compared to the known prodrug Glutaryl-Ser-Ala-Ser-Chg-Gln-Ser-Leu-Dox (SEQ ID NO: 1) (wherein Chg is cyclohexylglycine).

In one aspect the disclosure provides compounds represented by Formula I:

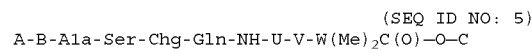
(SEQ ID NO: 5)
A-B-Ala-Ser-Chg-Gln-NH-U-V-W(Me)$_2$C(O)-O-C wherein:

A is GABA, Glutaryl or Y;

Y is an N-capping group;

B is ←mGly, Ser, ←DSer-ψ[NH—CO—NH] or X;

X is any amino acid residue;

U, if present, is Ser or i-Ser,

V, if present, is O, provided that at least one of U and V is present;

W is CH$_2$ or NH;

Chg is cyclohexylglycine; and

C is a chemotherapeutic agent or prostate disease drug.

In some embodiments, the disclosure is directed to an ester prodrug designed for PSA activation. In some embodiments, the ester prodrug is a chemotherapeutic prodrug. In other embodiments, the ester prodrug is a target-selective chemotherapeutic prodrug. In yet other embodiments, the ester prodrug comprises a PSA-cleavable peptide with the PSA-specific cleavage site located at the carboxyl end of glutamine (Gln).

In some embodiments, the peptide sequences are capable of rapid cleavage by PSA. In some embodiments, the peptide sequence comprises Formula IV:

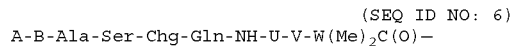
(SEQ ID NO: 6)
A-B-Ala-Ser-Chg-Gln-NH-U-V-W(Me)$_2$C(O)- wherein A is GABA, Glutaryl or Y;

Y is an N-capping group;

B is ←mGly, Ser, ←DSer-ψ[NH—CO—NH]— or X;

X is any amino acid residue;

U, if present, is Ser, or is i-Ser,

V, if present, is O, provided that at least one of U and V is present;

W is $CH_2$ or NH; and

Chg is cyclohexylglycine.

In some embodiments, the PSA-cleavable peptide comprises a self-immolative moiety (U-V-W(Me)$_2$C(O)—) that enables the release of free drug through chemical cyclization when incorporated into a prodrug. In some embodiments, the PSA-cleavable peptide is coupled to the C-14 α-hydroxyl of doxorubicin, an anthracycline with a similar hydroxyketone group, or a free hydroxyl of other chemotherapeutic agents. In other embodiments, the anthracycline comprises epirubicin. In still other embodiments, the anthracycline comprises pirarubicin. In yet other embodiments, the anthracycline comprises N-acetylated analogues such as TAN-1120 (U.S. Pat. No. 5,147,860).

In some embodiments, the ester prodrug comprises a chemotherapeutic agent. In some embodiments, the chemotherapeutic agent comprises paclitaxel. In other embodiments, the chemotherapeutic agent comprises thapsigargin. In yet other embodiments, the chemotherapeutic agent comprises doxorubicin. In still other embodiments, the chemotherapeutic agent comprises vinblastine. In further embodiments, the chemotherapeutic agent comprises an anthracycline. In other embodiments, the chemotherapeutic agent comprises epirubicin. In still other embodiments, the chemotherapeutic agent comprises pirarubicin. In yet other embodiments, the chemotherapeutic agent comprises N-acetylated anthracycline analogues such as TAN-1120.

In some embodiments, the ester prodrug comprises a prostate disease drug. In one embodiment, the prostate disease drug comprises silodosin. In another embodiment, the prostate disease drug comprises minoxidil (or sulfate metabolite). In still another embodiment, the prostate disease drug comprises prazosin (via functionalization). In yet another embodiment, the prostate disease drug comprises doxycycline.

In some embodiments, the present disclosure is directed to a method of administering to a subject in need thereof a therapeutically effective amount of a prodrug disclosed herein. In some embodiments, the method is to treat prostate disease. In other embodiments, the method is to treat prostate cancer.

Further provided is the use of a compound of Formula I and/or Formula IV in the manufacture of a medicament, in particular a medicament for the treatment of prostate cancer or prostate disease, especially a medicament for the treatment of prostate cancer. In some instances, the use of a compound of Formula I and/or Formula IV in the manufacture of a medicament for the prophylaxis of prostate disease is provided, especially the prophylaxis of prostate cancer.

Furthermore, the disclosure relates to a method for manufacturing compounds of Formula I and/or Formula IV, to novel intermediates of use in the manufacture of compounds of Formula I and/or Formula IV and to the manufacture of such intermediates.

In a further aspect, the disclosure provides pharmaceutical compositions comprising a compound of Formula I and/or Formula IV in association with a pharmaceutically acceptable adjuvant, diluent, excipient or carrier. The pharmaceutical composition will typically contain an effective amount (e.g. for humans) of the compound of Formula I and/or Formula IV, although sub-therapeutic amounts of the compound of Formula I and/or Formula IV may nevertheless be of value when intended for use in combination with other agents or in multiple doses.

The skilled person will recognize that references to a compound of Formula I and/or Formula IV will include any subgroup of the compounds of Formula I and/or Formula IV described herein.

V. BRIEF DESCRIPTION OF THE FIGURES

Figure 3:
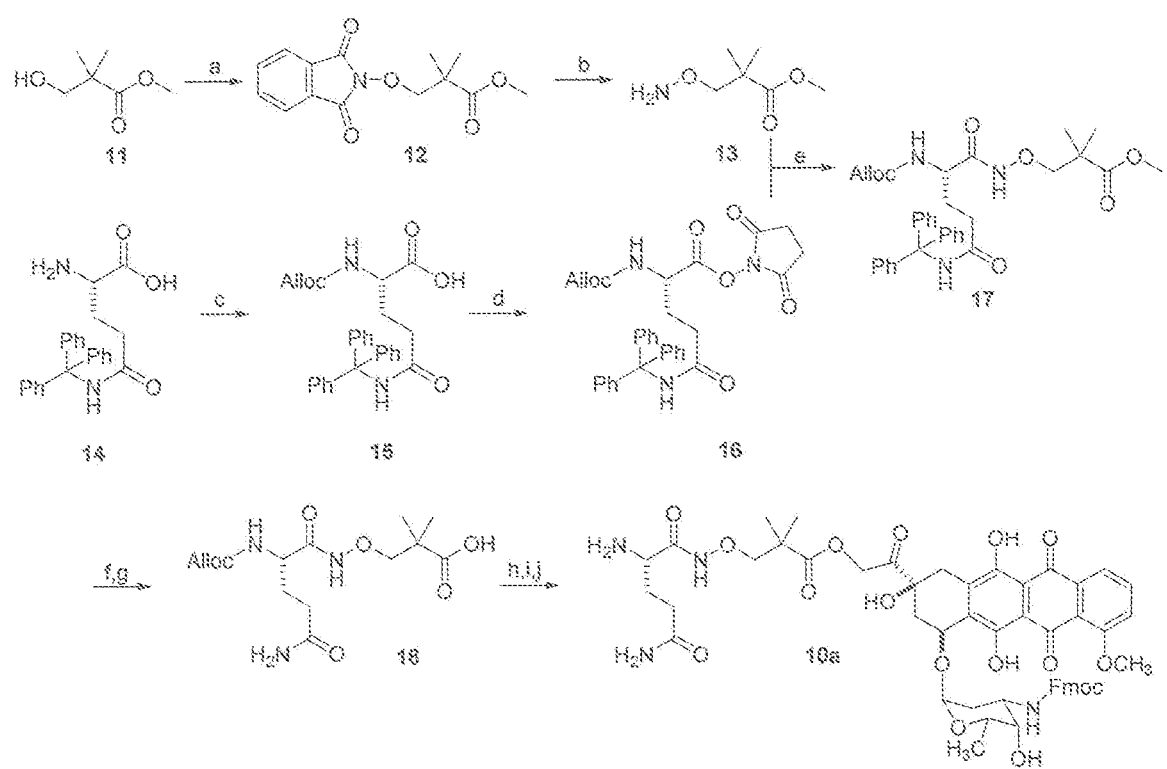

FIG. 3 represents synthesis of the aminoxypropionate-Doxorubicin ester Conjugate 10a. Reagents and conditions: (a) PhtOH, Ph$_3$P, DIAD, THF, 0° C. to room temperature (rt), 24 hours (h.); (b) H$_2$NNH$_2$, Et$_2$O, rt, 2 h; (c) allyl chloroformate, 10% K$_2$CO$_3$/MeCN (1:2), rt, 10 min; (d) EDC, HOSu, MeCN, rt, 2 h; (e) rt, 24 h; (f) 0.1 NaOH/THF, rt, 24 h; (g) 95% TFA/DCM, 0° C., 5 min; (h) 14-bromodaunorubicin (20), NaHCO$_3$ (1 equivalent (eq.)), 3 Å mol. sieves, acetone, rt, 72 h; (i) Fmoc-OSu, NaHCO$_3$, MeCN, rt, 1 h; j) tetrakis(triphenyl-phosphine)palladium(0)/dimedone, THF, rt, 1 h.

Figure 4:
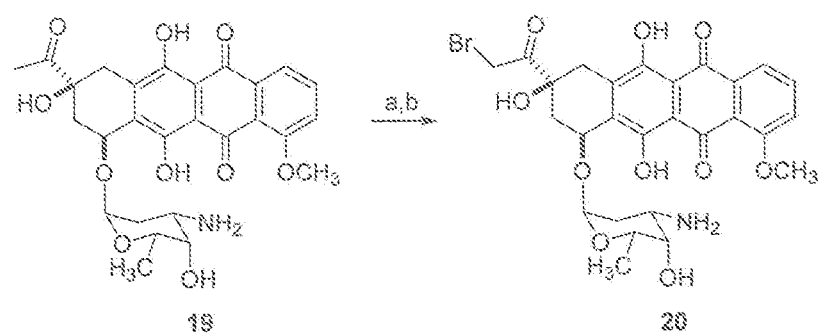

FIG. 4 represents synthesis of 14-bromodaunorubicin 20. Reagents and conditions: (a) HC(MeO)$_3$, Dioxane/MeOH (2;1), rt, 20 min; (b) Br$_2$/CHCl$_3$, rt, 40 min.

Figure 5:
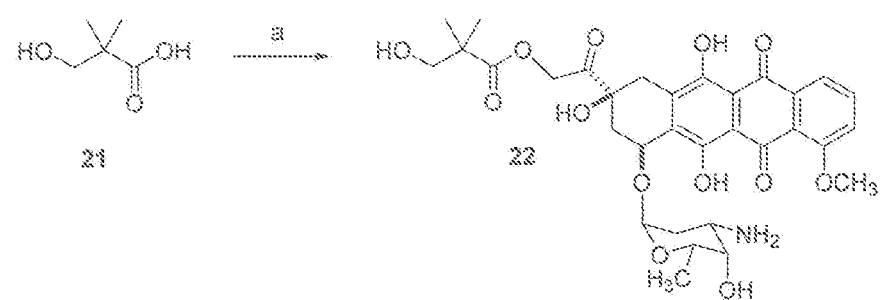

FIG. 5 represents synthesis of hydroxypivalate doxorubicin-14-O-ester. Reagents and conditions: (a) 21, NaHCO$_3$ (1 eq.), 3 Å mol. sieves, acetone, 50° C., 1 h.

Figure 6:
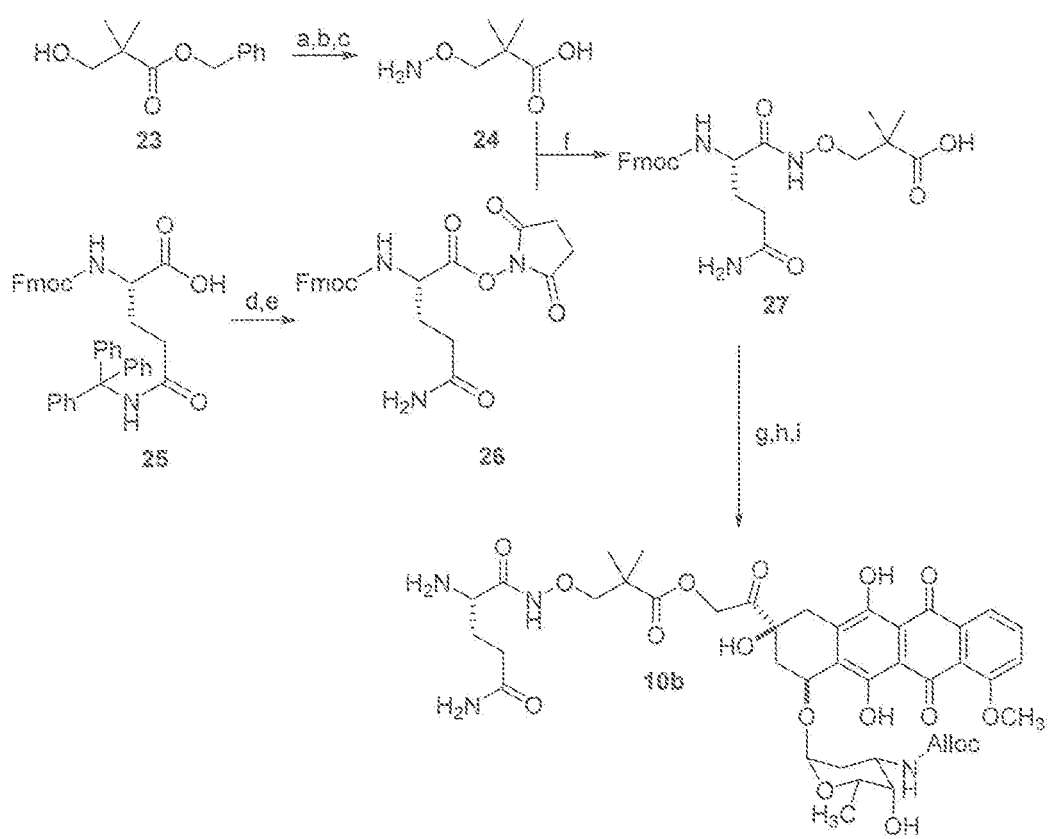

FIG. 6 represents synthesis of the aminoxypropionate-Doxorubicin ester Conjugate 10b. Reagents and conditions: (a) PhtOH, Ph$_3$P, DIAD, THF, 0° C. to rt, 24 h; (b) H$_2$/Pd—C, MeOH, rt, 5 h; (c) H$_2$NNH$_2$, Et$_2$O, rt, 2 h; (d) EDC, HOSu, MeCN, rt, 2 h; (e) 95% TFA/MeCN, rt, 5 min; (f) rt, 24 h; (g) 20, NaHCO$_3$ (1 eq.), 3 Å mol. sieves, acetone, rt, 72 h; (h) Alloc-OSu, NaHCO$_3$, MeCN, rt, 1 h; (i) 1% DBU, DMF, rt, 10 min.

Figure 7:
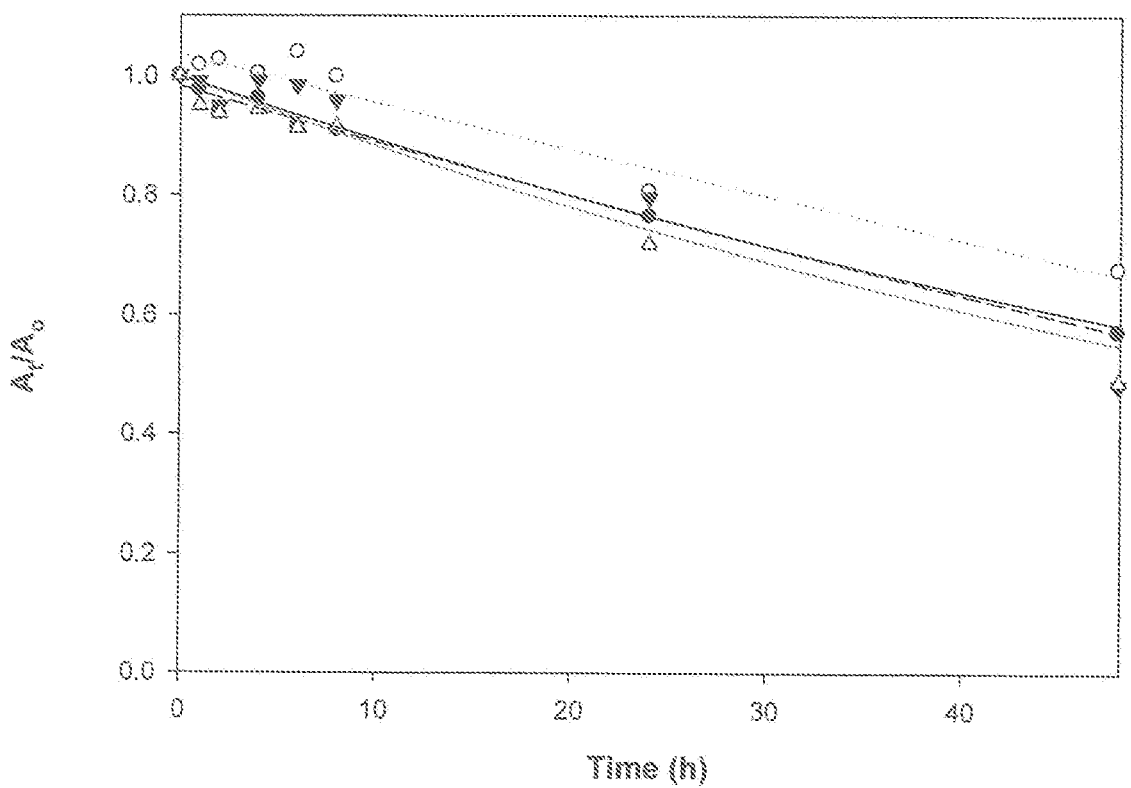

FIG. 7 represents stability of doxorubicin prodrugs in Tris Buffer. Each conjugate (100 μM) was incubated in 50 mM Tris/HCl buffer, pH 8.0 containing 10 mM CaCl$_3$ and 0.1% TWEEN-20 at 37° C. L-377202 (--●--), 2 (·· ○···), 3 (----▼----), 4 (----▽----)

Figure 8:
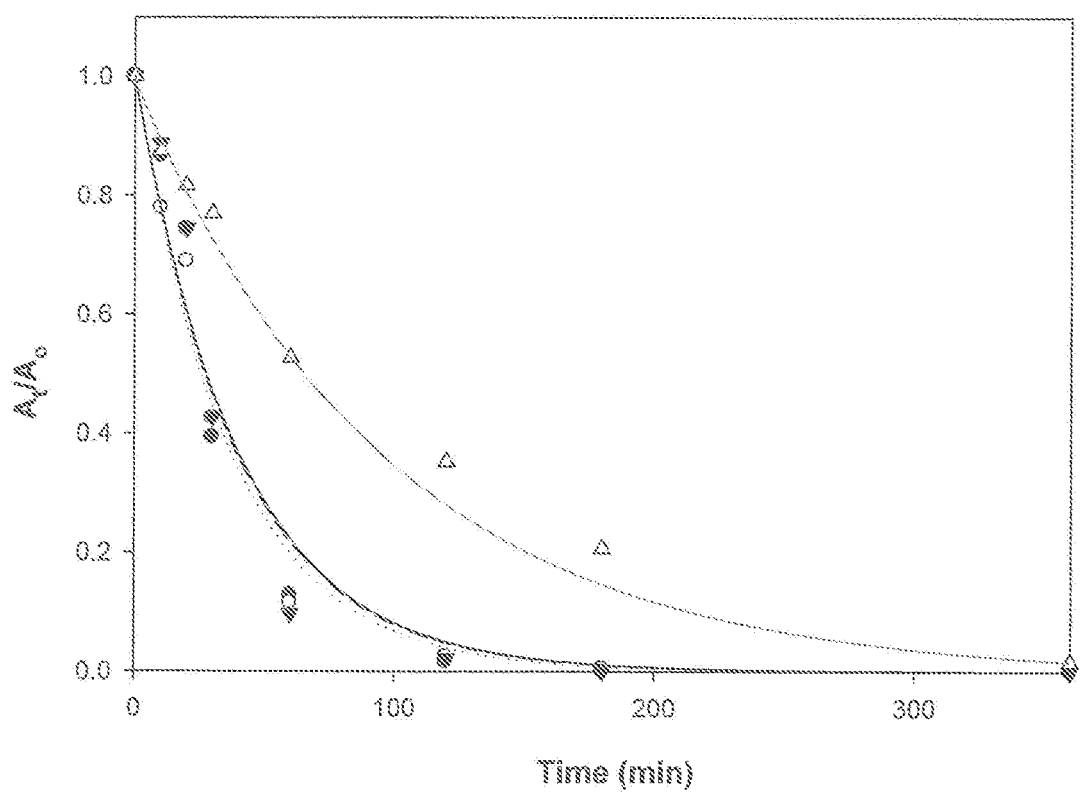

FIG. 8 represents disappearance of doxorubicin prodrugs during PSA hydrolysis. Each conjugate (1 • M) was incubated with PSA (1 • M) in 50 mM Tris/HCl buffer, pH 8.0 containing 10 mM CaCl$_2$ and 0.1% TWEEN-20 at 37° C. L-377202 (--●--), 2 (·· ○···), 3 (----▼----), 4 (----▽----)

Figure 9:
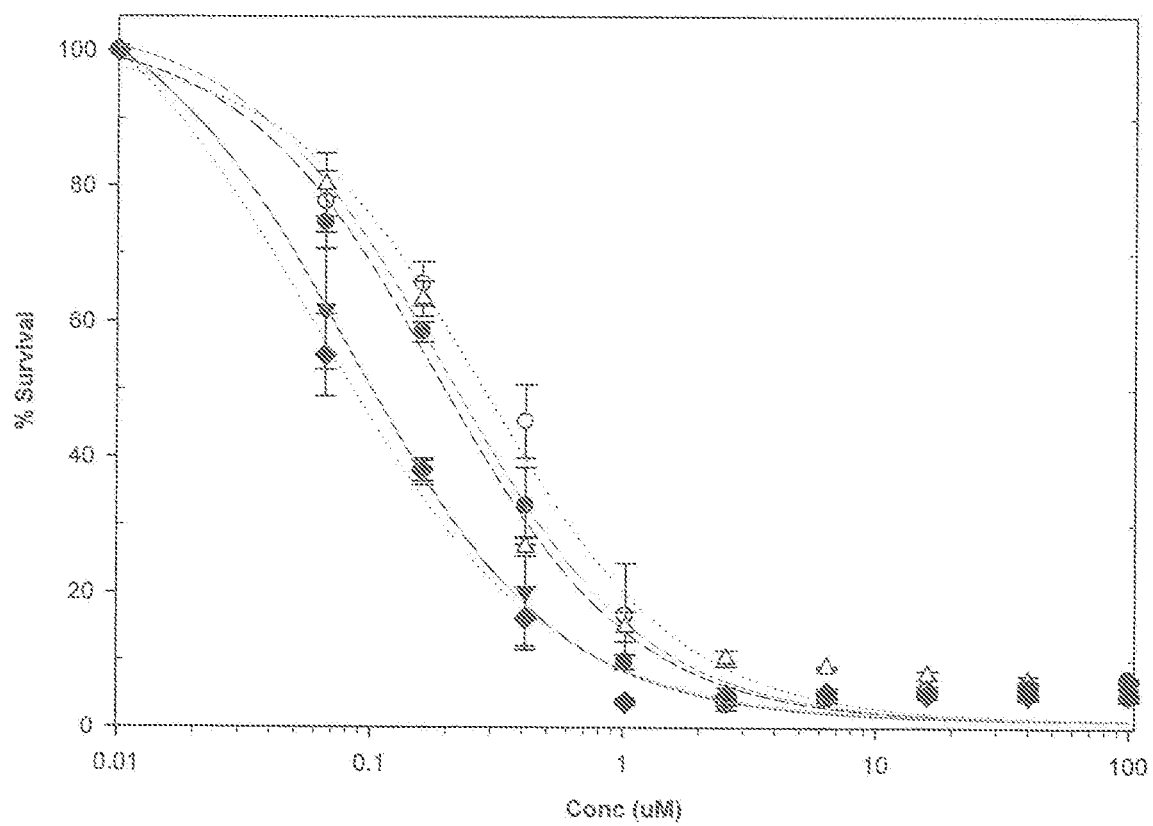

FIG. 9 represents cytotoxicity of doxorubicin prodrugs in LNCaP Cells. Doxorubicin (···◆···), L-377202 (--●--), 2 (·· ○···), 3 (----▼----), 4 (----▽----)

Figure 10:
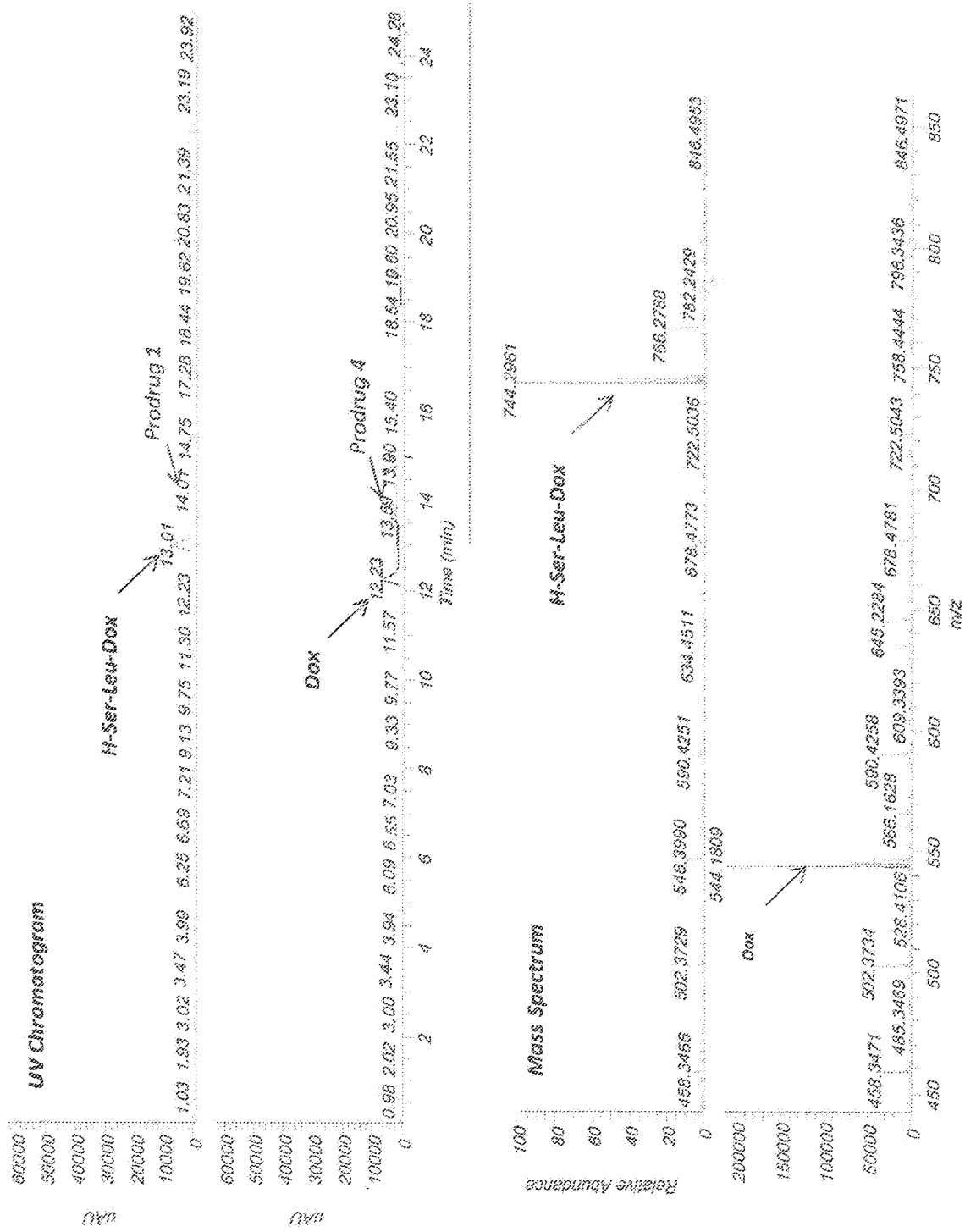

FIG. 10 represents PSA-mediated hydrolysis of prodrugs 1 and 4. Conditions: Each peptide conjugate (1 μM) was incubated with human PSA (1 μM) in 50 mM Tris/HCl buffer, pH 8, for 4 h. Samples were precipitated with 1 volume of ACN, centrifuged and analyzed by LC-MS-UV.

Figure 11:
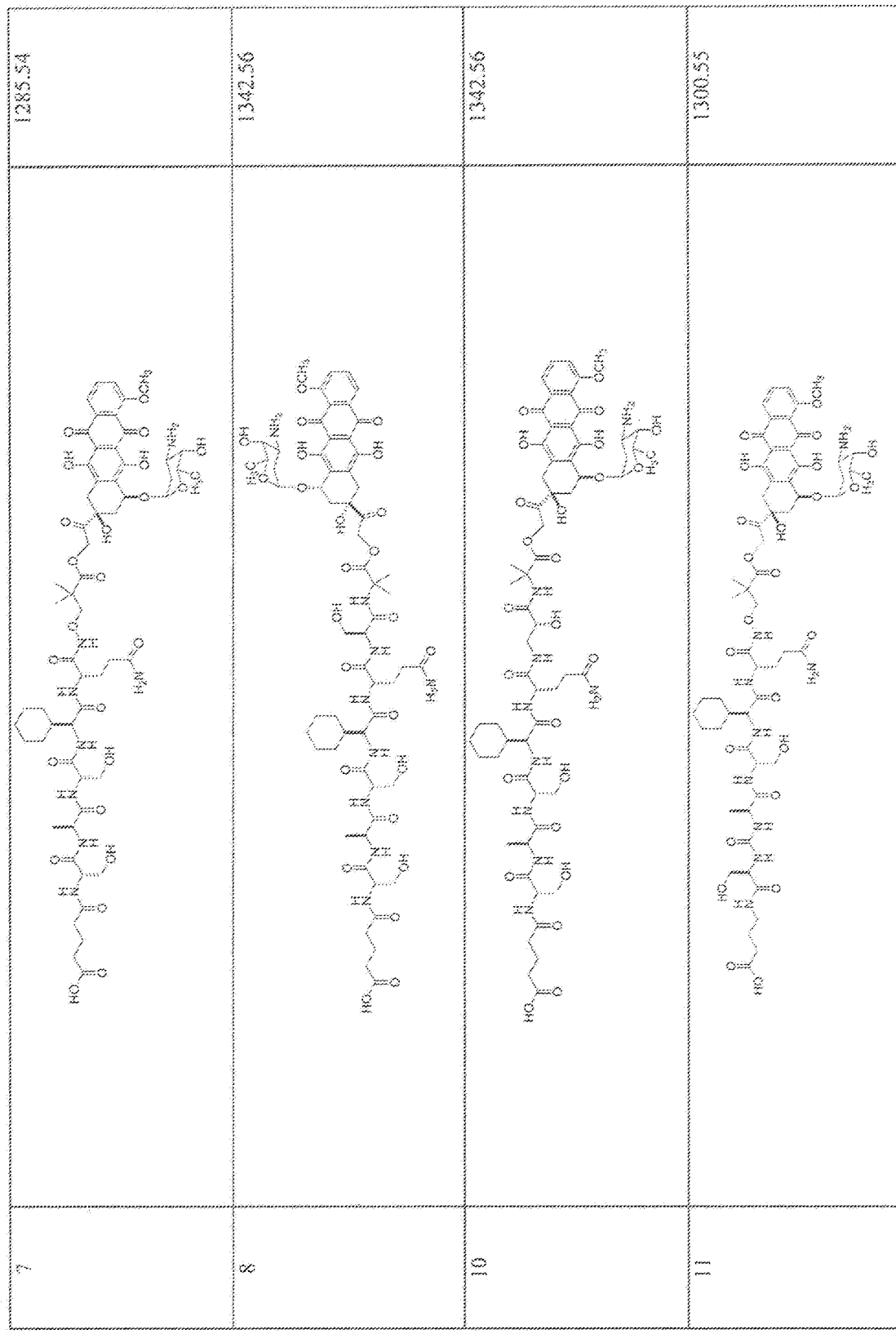
Figure 11:
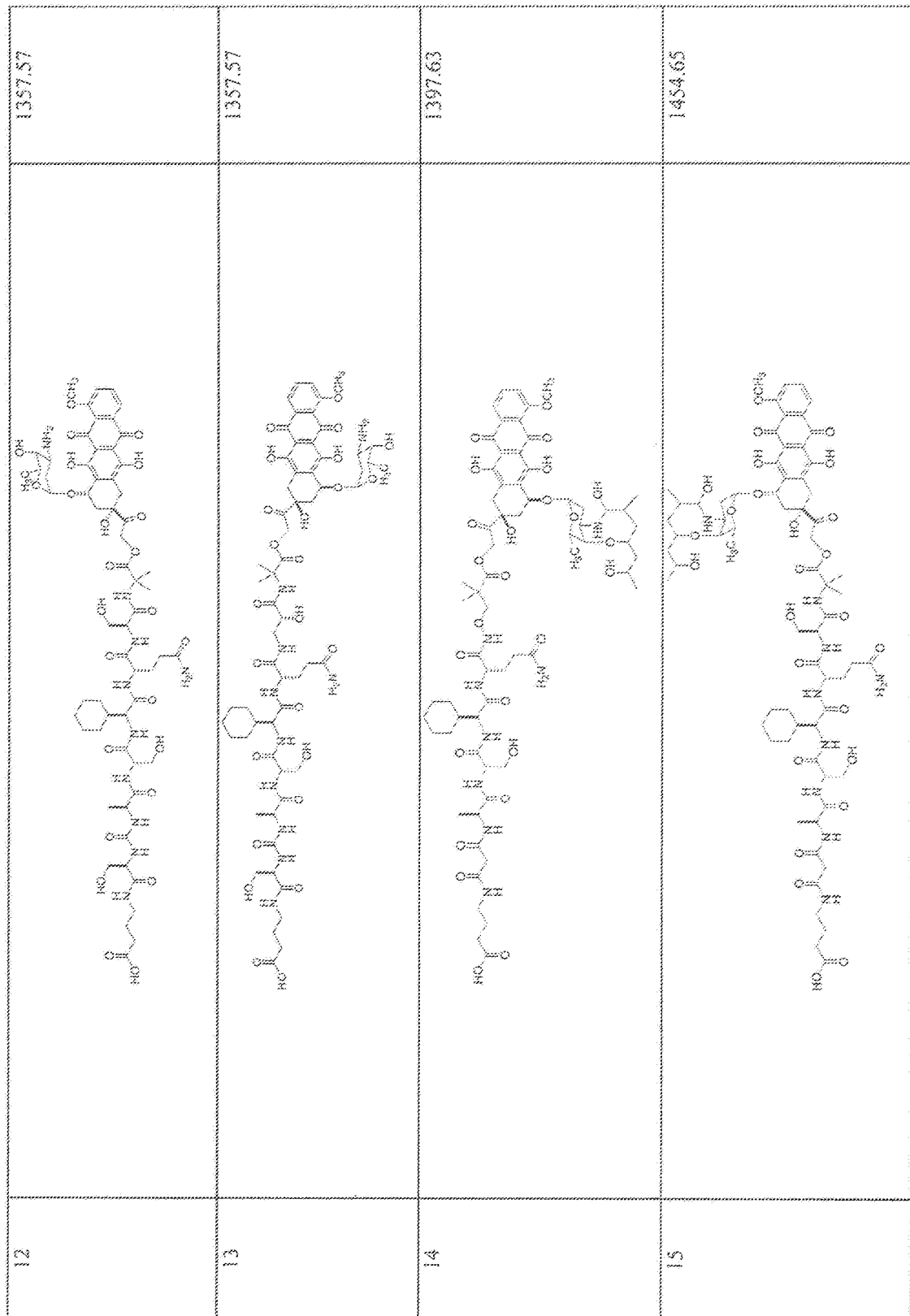
Figure 11:
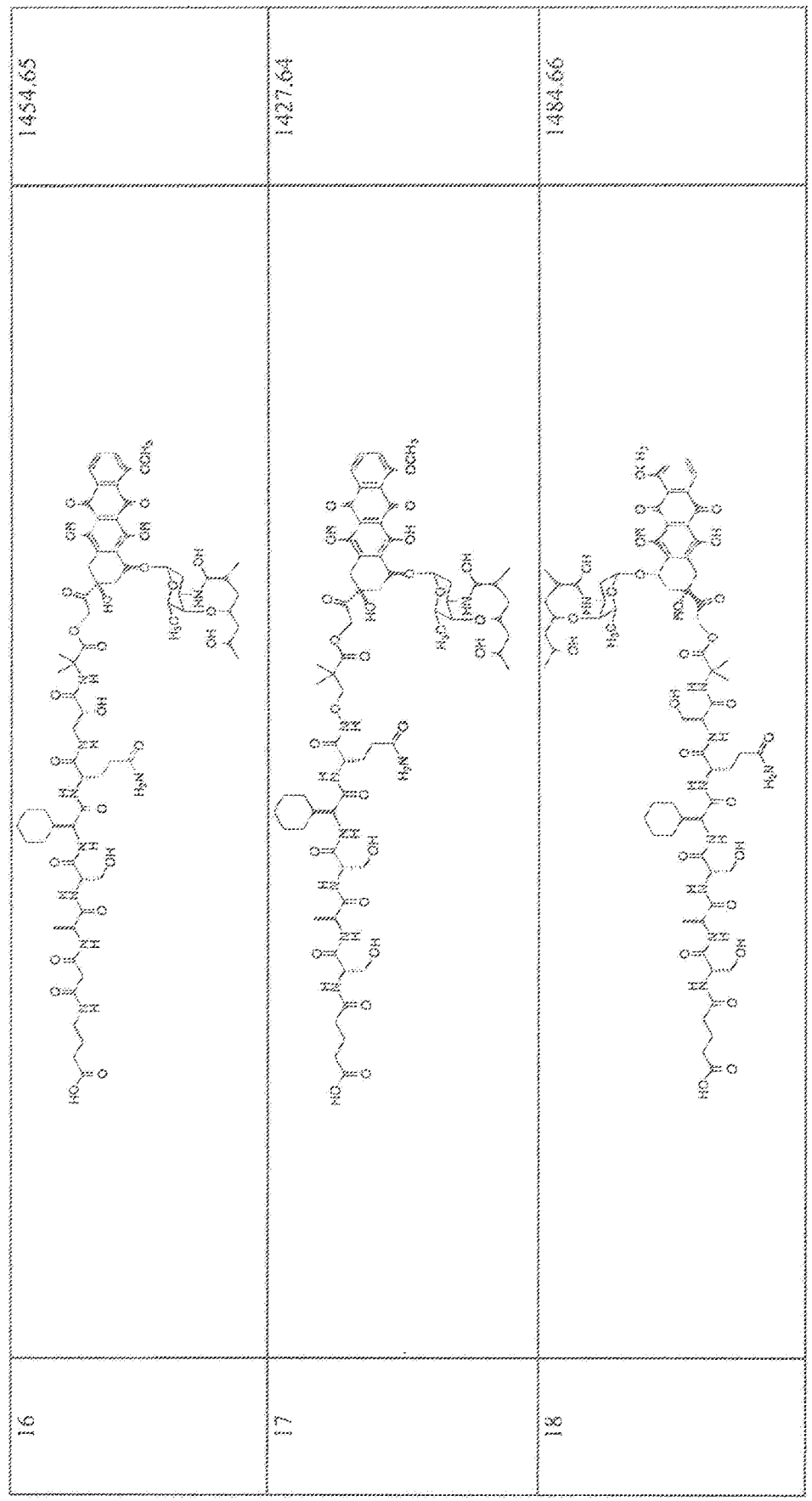
Figure 11:
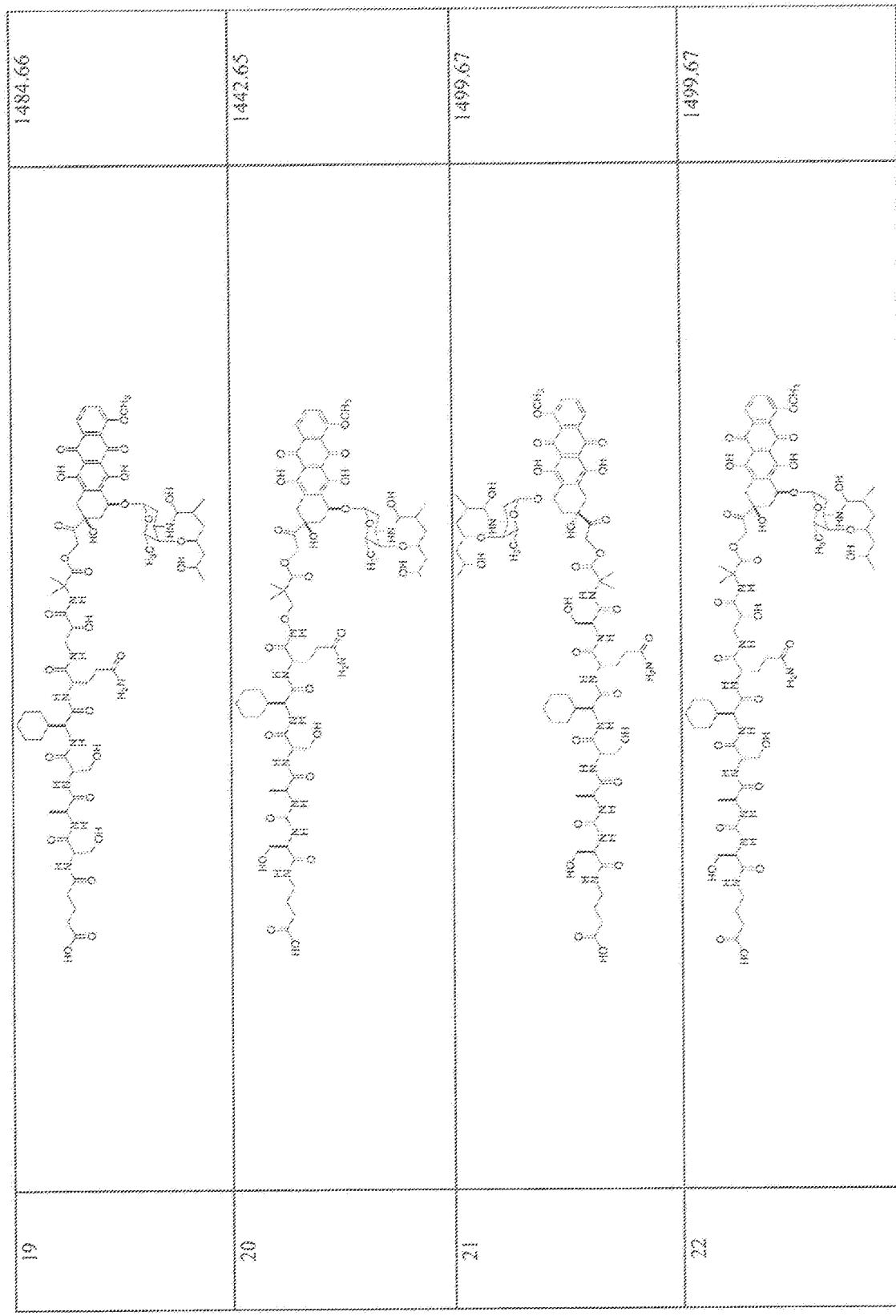

FIG. 11 represents a subset of compounds according to Formula I, along with mass spectrometry (MS) values based on positive ion mode $(M+H)^+$.

VI. DESCRIPTION

Definitions

The terms "treating" and "treatment" of a state, disorder, disease or condition as used herein refer to (1) delaying the appearance of clinical symptoms of the state, disorder, disease or condition developing in a patient that may be afflicted with or predisposed to the state, disorder, disease or condition, (2) inhibiting the state, disorder, disease or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a patient to be treated is either statistically significant or at least perceptible to the patient and/or to the physician.

The term "prophylaxis" of a state, disorder, disease or condition as used herein refers to prevention of the appearance of clinical symptoms of the state, disorder, disease or condition developing in a patient that is predisposed to the state, disorder, disease or condition.

The terms "effective amount" and "therapeutically effective amount" as used herein refer to the amount of a compound that, when administered to a patient for treating a state, disorder, disease or condition, is sufficient to affect such treatment. The effective amount or therapeutically effective amount will vary depending on the compound, the disease and its severity, and the age, weight, physical condition and responsiveness of the individual to be treated.

The terms "delivering" and "administering" as used herein refer to providing a therapeutically effective amount of an active agent to a particular location or locations within a patient causing a therapeutically effective concentration of the active ingredient at the particular location or locations. For example, this can be accomplished by local (intratumoral) or systemic (intravenous) administration of the active ingredient to the host, among others.

The term "composition" or "pharmaceutical composition" as used herein refers to a product comprising the specified agent or agents, as well as any product which results, directly or indirectly, from combination of the specified ingredients. The terms are intended to include the combination of an active agent or agents with a suitable pharmaceutical carrier, inert or active, making the composition suitable for diagnostic or therapeutic use in vivo, in vitro or ex vivo. The compositions and pharmaceutical composition can also include pharmaceutically acceptable stabilizers, preservatives, adjuvants, fillers, flavors and other excipients.

As used herein and in the appended claims, the singular forms "a," "and," and "the" include plural references unless the context clearly dictates otherwise.

The terms "peptide" and "protein" are used interchangeably herein to refer to a polymer with at least one naturally occurring or synthetic amino acid residue. The term encompasses amino acid chains of any length and also includes compounds that include moieties other than amino acids.

The term "PSA-cleavable peptide" specifically refers to a peptide that includes a cleavage site for a tumor specific enzyme, e.g. PSA, chymotrypsin, human tissue kallikrein 7 (hK7), and the like.

In addition to the definitions above, the following abbreviations are used in the examples and synthetic schemes below and in the figures. If an abbreviation used herein is not defined, it has its generally accepted meaning.
Ac Acetyl
ACN Acetonitrile
Ala Alanine
Alloc Allyloxycarbonyl
Bn Benzyl
Boc t-Butoxycarbonyl
Bu Butyl
Cbz Benzoxyarbonyl
Chg Cyclohexylglycine
DBU 1,8-Diazabicycloundec-7-ene
DCM Dichloromethane
DEA Diethylamine
DIAD Diisopropyl azodicarboxylate
DIEA Diisopropylethylamine
DMAP 4-Dimethylaminopyridin
DMF N,N-Dimethylformamide
DMSO Dimethyl sulfoxide
Dox Doxorubicin
EDA Ethylenedamine
EDC 1-(3-Dimethylaminopropyl)-3-ethylcarbodiimide hydrochloride
$Et_2O$ Diethyl ether
EtOAc Ethyl acetate
FBS Fetal bovine serum
FCC Flash column chromatography
Fm 9-Fluorenylmethyl
Fm-GABA 9-Fluoromethyl-4-aminobutyric acid
Fmoc 9-Fluorenylmethyloxycarbonyl
GABA 4-Aminobutyric acid
Gln Glutamine
HATU 1-[Bis(dimethylamino)methylene]-1H-1,2,3-triazolo[4,5-b]pyridinium 3-oxid hexfluorophosphate
$HC(MeO)_3$ Trimethylorthoformate
HBTU 2-(1H-benzotriazole-1-yl)-1,1,3,3-tetramethyluronium
HOBt 1-Hydroxybenzotriazole
HOSu N-Hydroxysuccinimide
Hyp trans-4-Hydroxyproline
IP Intraperitoneal
IPCF Isopropyl chloroformate
IS Internal Standard
IV Intravenous
LC Liquid chromatography
LC-MS Liquid chromatography-mass spectrometry
Leu Leucine
Lys Lysine
MeCN Acetonitrile
MeOH Methanol
MS Mass spectrometry
MSNT 1-(Mesitylene-2-sulfonyl)-3-nitro-1H-1,2,4-triazole
MTD Maximum tolerated dose
MTT 3-(4,5-Dimethylthiazol-2-yl)-2,5-diphenyltetrazolium bromide
NMP N-Methylpyrolidone
OSu ester N-hydroxysuccinimide ester
Phe Phenylalanine
$Ph_3P$ Triphenylphosphine
PhtOH Phthallic acid
PSA Prostate-specific antigen
PyBOP Benzotriazol-1-yl-oxytripyrrolidinophosphonium hexafluorophosphate
Ser Serine
SRM Selected-reaction monitoring
TFA Trifluoroacetic acid
THF Tetrahydrofuran
TLC Thin-layer chromatography
Trt Trityl
UV Ultraviolet Unless defined otherwise, all technical and scientific terms used herein have the same meaning as commonly understood by one of ordinary skill in the art to which this invention belongs. All publications mentioned herein are incorporated herein by reference in their entireties.

Compounds and Compositions

Peptides provide substrates for proteolytic cleavage by enzymes. The present disclosure relates to PSA-targeted chemotherapeutic ester prodrugs that are both PSA-specific and readily cleaved by the PSA protease. Generally, the ester prodrugs are comprised of a chemotherapeutic agent (-C) and a PSA-cleavable peptide (A-B-Ala-Ser-Chg-Gln-NH-U-V-W(Me)₂C(O)—) (SEQ ID NO: 6), and are represented according to Formula I:

Formula I
(SEQ ID NO: 5)
A-B-Ala-Ser-Chg-Gln-NH-U-V-W(Me)₂C(O)—O—C wherein:
A is GABA, Glutaryl or Y;
Y is an N-capping group;
B is ←mGly, Ser, ←DSer-ψ[NH—CO—NH] or X;
X is any amino acid residue;
U, if present, is Ser or i-Ser,
V, if present, is O, provided that at least one of U and V is present;
W is CH₂ or NH;
Chg is cyclohexylglycine; and
C is a chemotherapeutic agent or prostate disease drug.

Formula II represents one subset of compounds of Formula I:

Formula II
(SEQ ID NO: 8)
A-B-Ala-Ser-Chg-Gln-NH-V-W(Me)₂C(O)—O—C wherein:
A is GABA, Glutaryl or Y;
Y is an N capping group;
B is ←m mGly, Ser, ←m DSer-ψ[NH—CO—NH]— or X;
X is any amino acid residue;
V is O;
W is CH₂;
Chg is cyclohexylglycine; and
C is a chemotherapeutic agent or prostate disease drug.

Formula III represents a second subset of compounds of Formula I:

Formula III
(SEQ ID NO: 9)
A-B-Ala-Ser-Chg-Gln-NH-U-W(Me)₂C(O)—O—C wherein:
A is GABA, Glutaryl or Y;
Y is an N-capping group;
B is ←m mGly, Ser, ←m DSer-ψ[NH—CO—NH]— or X;
X is any amino acid residue;
U is Ser, or is i-Ser;
W is NH;
Chg is cyclohexylglycine; and
C is a chemotherapeutic agent or prostate disease drug.

The PSA-cleavable peptides can be generally represented by Formula IV:

Formula IV
(SEQ ID NO: 6)
A-B-Ala-Ser-Chg-Gln-NH-U-V-W(Me)₂C(O)— wherein:
A is GABA, Glutaryl or Y;
Y is an N-capping group;
B is ←m mGly, Ser, ←m DSer-ψ[NH—CO—NH]— or X;
X is any amino acid residue;
U, if present, is Ser, or is i-Ser,
V, if present, is O, provided that at least one of U and V is present;
W is CH₂ or NH; and
Chg is cyclohexylglycine.

The peptides may be synthesized by any known technique used in the art. For example, they may be synthesized by standard solid-phase peptide synthesis (Barany and Merrifield, The Peptides 2:1 284, Gross and Meienhofer, Eds., Academic Press, New York) using tert-butyloxycarbonyl amino acids and phenylacetamidomethyl resins (Mitchell et al. (1978) *J. Org. Chem.* 43:2845-2852) or 9-fluorenylmethyloxy-carbonyl amino acids on a polyamide support (Dryland and Sheppard (1986) *J. Chem. So. Perkin Trans.* I, 125 137). Alternatively, synthetic peptides can be prepared by pepscan synthesis (Geysen et al. (1984) *J. Immunol. Methods* 03:259 (1987); Geysen et al. (1984) *Proc. Natl. Acad. Sci. USA* 81:3998, Cambridge Research Biochemicals, Cambridge, U.K.) or by standard liquid-phase peptide synthesis.

Peptides may also include a protective group on their amino-end. Suitable examples include Carbobenzyloxy (Cbz) group, tert-Butyloxycarbonyl (BOC) group, 9-Fluorenyl-methyloxycarbonyl(FMOC) group, Benzyl(Bn) group, p-methoxyphenyl (PMP) group, Benzyloxy-carbonyl (Z) group, and glutaryl. The use of amino-protecting groups in peptide synthesis is known and is described in, for example, Protective Groups in Organic Chemistry (1973) McOmie, ed., Plenum Press, NY; and Protective Groups in Organic Synthesis (1981) Green ed., John Wiley & Sons, NY, incorporated herein by reference in their entirety.

In some embodiments the peptides in Formula I and/or Formula IV contain an N-capping group designed to mitigate premature cleavage by aminopeptidases in the body. Suitable N-capping groups include GABA, glutaryl, succinyl, malonyl and acetyl.

In one embodiment, peptides are provided that include a cleavage site specifically recognized by the prostate specific antigen (PSA). The term "prostate specific antigen" as used herein includes PSA itself, pharmaceutically acceptable salts of PSA, and other proteases such as chymotrypsin and human tissue kallikrein 7 (hK7) that have the same or substantially the same proteolytic cleavage activity and specificity as PSA. It is known that the PSA cleavage site is located at the carboxyl end of a glutamine or a hydrophobic amino acid like tyrosine, phenylalanine, leucine and isoleucine. Accordingly, a glutamine or a hydrophobic amino acid, and more preferably glutamine, is located at P1.

The length of the peptide and its water solubility are also an important consideration when constructing the peptide for use in the methods and compositions claimed herein, as they are known to play a role in the ability of PSA and other enzymes to cleave the peptide. Accordingly, the PSA-cleavable peptides are designed to increase their hydrophilic properties and include at least 3 amino acids to achieve an adequate balance between polarity and PSA binding affinity. The hydrophilic properties of the peptides can be modulated by amino acid side chain polarity. Using predictive in silico tools as a guide, such as log D calculations, the desired hydrophilicity (and hence solubility) can be incorporated into the peptide sequence by design. Generally, a peptide's water solubility can be improved by selecting hydrophilic amino acids or attaching hydrophilic compounds to the peptide.

Coupling of the PSA-cleavable peptide to a readily accessible hydroxyl group is critical for releasing the free drug through chemical cyclization. For example, coupling the PSA-cleavable peptide to the C-14 α-hydroxyl of doxorubicin, TAN-1120, etc. Following PSA hydrolysis, the self-immolative moiety of the peptide efficiently releases free chemotherapeutic agents from the peptide through non-enzymatic cyclization without cytotoxicity inhibiting fragments that remain attached to the chemotherapeutic agent (such as Leu in Leu-Doxorubicin which is released from L-377,202). This is specifically achieved by coupling the carboxyl end of the self-immolative moiety to a readily accessible hydroxyl group of the chemotherapeutic agent or drug through chemical synthesis.

Chemotherapeutic agents may include cytotoxic agents. Cytotoxic agents inhibit or prevent the function of cells and/or cause destruction of cells. Examples of chemotherapeutic and/or cytotoxic agents include, without limitation, paclitaxel, thapsigargin, vinblastine, doxorubicin, anthracyclines (e.g. epirubicin, pirarubicin), N-acetylated anthracycline analogues such as TAN-1120 (U.S. Pat. No. 5,147,860), and other cytotoxic agents with a free hydroxyl/hydroxyketone functional group.

The combinations of PSA-cleavable peptide and chemotherapeutic agents may find use in the manufacture of a medicament for treating prostate cancer and/or prostate disease in a mammal infected therewith, said combination in particular comprising a compound of Formula I, as specified above. Or the disclosure provides a method of treating a mammal, in particular a human, suffering from prostate disease or prostate cancer comprising the administration to said mammal an effective amount of a combination as specified herein. In particular, the treating comprises the local or systemic administration of the combination, and an effective amount is that amount which is effective in treating the clinical conditions associated with prostate disease or prostate cancer.

Pharmaceutical compositions may be administered in a manner appropriate to the type of disease being treated or prevented, such as prostate cancer or other prostate diseases, as determined by persons skilled in the art. In one embodiment, the composition may be administered parenterally. Examples of parenteral administration are subcutaneous, intravenous, intramuscular, intradermal, intrathecal, intraocular, transdermal, and general infusion techniques. Additionally, oral administration of the peptide linked prodrugs described herein can be implemented using peptide drug delivery technologies and approaches such as absorption enhancers (e.g. chitosans), carrier systems (e.g. cellulose), stability enhancers (e.g. lipidization) and enzyme inhibitors (e.g. FT448) (see, for example, Bruno et al. (2013) *The Deliv.* 4(11):1443-1467). Administration of the peptide linked prodrug can also be accomplished via suppository.

Methods for preparation of pharmaceutical compositions are well known in the art (see, e.g., Remington's Pharmaceutical Sciences 16th Edition (1980) Easton: Mac Publishing Company). Pharmaceutical compositions comprising peptide conjugates may be prepared by methods including, e.g., conventional mixing, dissolving, emulsifying, encapsulating, entrapping, lyophilizing, and spray-drying.

Pharmaceutical compositions may be formulated in a conventional manner using one or more physiologically acceptable excipients, such as diluents, carriers, adjuvants, binders, fillers, salts, lubricants, glidants, disintegrants, coatings, coloring agents, etc. and auxiliaries that facilitate processing of the active agents into preparations that can be used pharmaceutically. Examples of such excipients include, but are not limited to, acacia, alginate, alginic acid, aluminum acetate, benzyl alcohol, butyl paraben, butylated hydroxy toluene, citric acid, calcium carbonate, candelilla wax, croscarmellose sodium, confectioner sugar, colloidal silicone dioxide, cellulose, plain or anhydrous calcium phosphate, carnuba wax, corn starch, carboxymethylcellulose calcium, calcium stearate, calcium disodium EDTA, copolyvidone, calcium hydrogen phosphate dihydrate, cetylpyridine chloride, cysteine HCL, crossprovidone, calcium phosphate di or tri basic, dibasic calcium phosphate, disodium hydrogen phosphate, dimethicone, erythrosine sodium, ethyl cellulose, gelatin, glyceryl monooleate, glycerin, glycine, glyceryl monostearate, glyceryl behenate, hydroxy propyl cellulose, hydroxyl propyl methyl cellulose, hypromellose, HPMC phthalate, iron oxides or ferric oxide, iron oxide yellow, iron oxide red or ferric oxide, lactose hydrous or anhydrous or monohydrate or spray dried, magnesium stearate, microcrystalline cellulose, mannitol, methyl cellulose, magnesium carbonate, mineral oil, methacrylic acid copolymer, magnesium oxide, methyl paraben, providone or PVP, PEG, polysorbate 80, propylene glycol, polyethylene oxide, propylene paraben, polaxamer 407 or 188 or plain, potassium bicarbonate, potassium sorbate, potato starch, phosphoric acid, polyoxy 140 stearate, sodium starch glycolate, starch pregelatinized, sodium crossmellose, sodium lauryl sulfate, starch, silicon dioxide, sodium benzoate, stearic acid, sucrose, sorbic acid, sodium carbonate, saccharin sodium, sodium alginate, silica gel, sorbiton monooleate, sodium stearyl fumarate, sodium chloride, sodium metabisulfite, sodium citrate dihydrate, sodium starch, sodium carboxy methyl cellulose, succinic acid, sodium propionate, titanium dioxide, talc, triacetin, and triethyl citrate.

Proper formulation is dependent upon the route of administration chosen. For example, formulations for parenteral administration may be presented in unit dosage form including, for example, ampoules and multi-dose containers, optionally with an added pharmaceutical preservative. The compositions may take such forms as suspensions, solutions, or emulsions in oily or aqueous vehicles, and may contain formulating materials such as suspending, stabilizing, and/or dispersing agents.

For injection, agents are typically formulated in aqueous solution, preferably in physiologically compatible buffers or physiological saline buffer. Suitable buffering agents include, e.g., trisodium orthophosphate, sodium bicarbonate, sodium citrate, N-methylglucamine, L(+)-lysine, and L(+)-arginine. Solutions of the active agents can be optionally mixed with a nontoxic surfactant. Dispersions can also be prepared in glycerol, liquid polyethylene glycols, triacetin, and mixtures thereof, and in oils. Under ordinary conditions of storage and use, these preparations may contain a preservative to prevent the growth of microorganisms.

Pharmaceutical dosage forms suitable for injection or infusion include, for example, sterile aqueous solutions or dispersions, or sterile powders including the active agent or agents that are adapted for the extemporaneous preparation of sterile injectable or infusible solutions or dispersions, optionally encapsulated in liposomes. In all cases, the ultimate dosage form is preferably sterile, fluid, and stable under the conditions of manufacture and storage. The proper fluidity can be maintained, for example, by the formation of liposomes, by the maintenance of the required particle size in the case of dispersions, or by the use of surfactants. In many cases, isotonic agents can be included, for example, sugars, buffers, or sodium chloride. Prolonged absorption of the injectable compositions can be brought about by the use of agents to delay absorption (e.g., aluminum monostearate, gelatin) in the compositions.

Sterile injectable solutions can be prepared by incorporating the active agent or agents in the required amount in the appropriate solvent with optional ingredients as required (e.g., as enumerated above), followed by, for example, filter sterilization. In the case of sterile powders for the preparation of sterile injectable solutions, methods of preparation include, for example, vacuum drying and freeze drying techniques, which yield a powder of the active ingredient plus any additional desired ingredient present in the previously sterile-filtered solutions.

Other parenteral administrations also include aqueous solutions of a water-soluble form, such as, without limitation, a salt of the active agent or agents. Additionally, suspensions of active agents may be prepared in a lipophilic vehicle. Suitable lipophilic vehicles include, for example, fatty oils such as sesame oil, synthetic fatty acid esters such as ethyl oleate and triglycerides, and materials such as liposomes. Aqueous injection suspensions typically contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

An oral composition can be any orally acceptable dosage form including, but not limited to, tablets, capsules, emulsions, and aqueous suspensions, dispersions, and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Suitable in vitro assays can be used to preliminarily evaluate the efficacy of the prodrug described herein, in inhibiting and/or treating prostate cancer and/or prostate disease. The prodrug described herein can further be examined for efficacy in treating and/or inhibiting prostate cancer and/or prostrate disease by in vivo assays. For example, the prodrugs described herein, can be administered to an animal (e.g., a mouse model) having prostate cancer and/or prostate disease and its therapeutic effects can be accessed. Based on the results, an appropriate dosage range and administration route for animals, such as humans, can also be determined.

Prodrug Design and Synthesis

Figure 1:
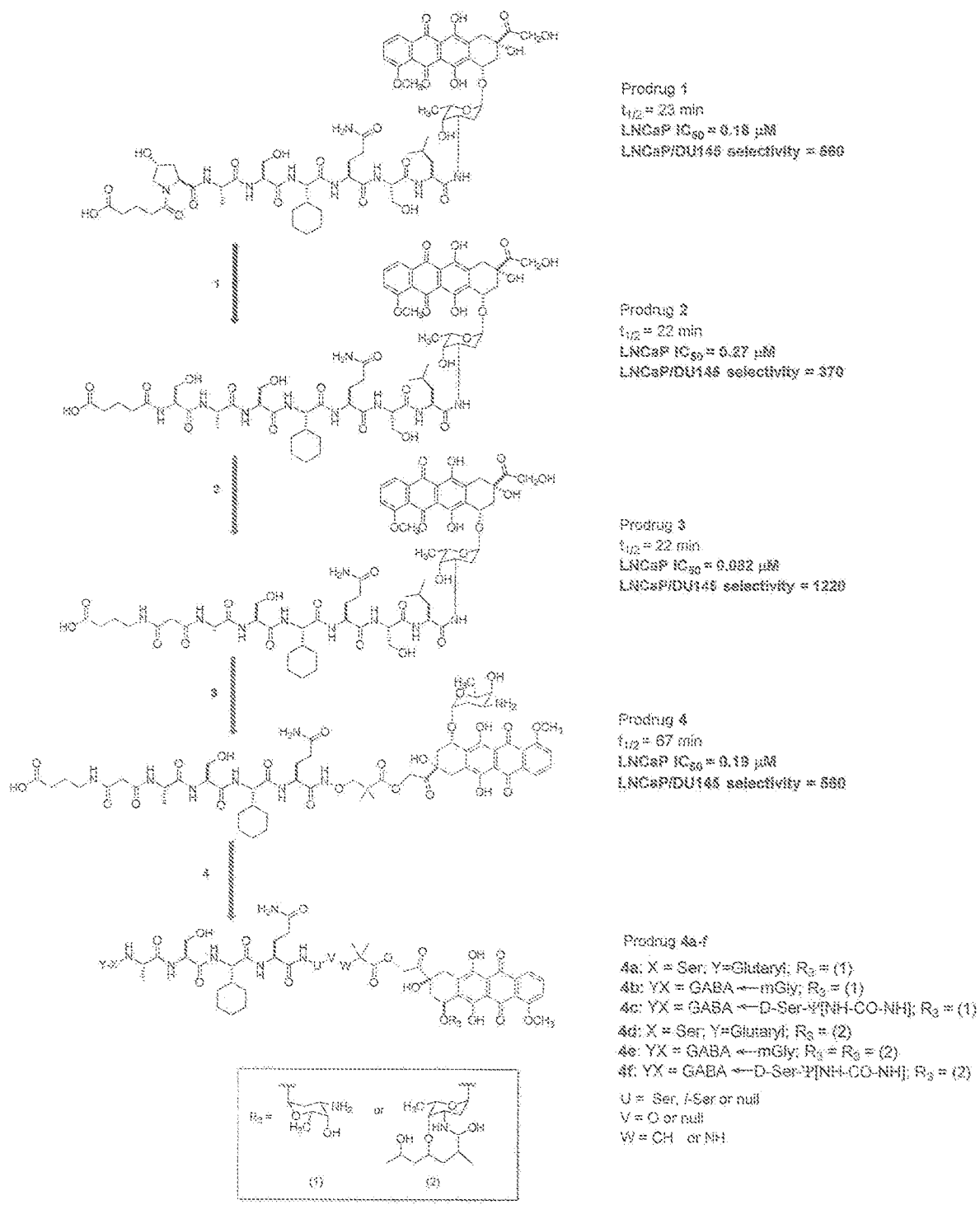
FIG. 1 represents prodrug design summary.

Prodrugs containing PSA-cleavable peptides attached to the aminoglycoside or C-14 α-hydroxyl of doxorubicin were prepared. All prodrugs were synthesized by convergent synthesis using the appropriate intermediates for ready attachment to various peptide sequences (see, for example, FIG. 1).

All chemicals and protected amino acids were purchased from Sigma-Aldrich (St. Louis, Mo.), Chem-Impex (Wood Dale, Ill.) or AAPPTEC (Louisville, Ky.). Solvents were either ACS reagent or HPLC grade and used without further purification. Prodrug 1 (Glutaryl-Hyp-Ala-Ser-Chg-Gln-Ser-Leu-Dox) (SEQ ID NO: 4) was supplied by Merck Sharpe & Dohme (Rahway, N.J.). For cytotoxicity cell-based assays, cell growth medium was prepared by adding L-glutamine (2 mM), fetal bovine serum (10%), penicillin G (100 units/mL) and streptomycin sulfate (100 units/mL) to phenol red-containing RPMI 1640. Reactions were monitored by TLC and/or on an LC-MS system consisting of PE 200 Series autosampler and pumps (Perkin Elmer, Waltham, Mass.) coupled to an LCQ ion trap mass spectrometer (Thermo Scientific, Waltham, Mass.). Flash column chromatography (FCC) was performed on a Teledyne ISCO CombiFlash Companion Automated Flash Chromatographic System (Teledyne Technologies, Thousand Oaks, Calif.) with pre-packed silica gel columns. Unless otherwise specified, HPLC purification of peptides and intermediates was carried out from $H_2O$/ACN containing 0.1% TFA. All $^1H$ and $^{13}C$ NMR spectra were recorded on a 400 MHz Bruker spectrometer at ambient temperature and calibrated using residual un-deuterated solvents as the internal reference. Accurate mass values of final peptide conjugates were determined by direct inlet infusion of 10 μg/mL solutions using a LTQ Orbitrap XL or Velos (Thermo Scientific, Waltham, Mass.). Metabolite identification was performed using an LTQ-Orbitrap mass spectrometer (Thermo Fisher, Waltham, Mass.) equipped with an electrospray source operated in positive ionization mode interfaced with Shimadzu LC-20ADXR pumps, a SIL-20ACXR autosampler and SPD-M20A diode array (Shimadzu, Columbia, Md.). Chromatographic separation was achieved with a 2.1×100 mm, 1.7 μm BEH C18 column (Waters Corporation, Huntingdon Valley, Pa.) using a water (A)/ACN (B) mobile phase system containing 0.1% formic acid (v/v) and UV detection at 254 and 484 nm. The gradient was performed at a total flow rate of 200 μL/min as follows, 2% B from 0 to 3 min, 2 to 95% B from 3 to 15 min, 95% B from 15 to 20 min, 95 to 2% B from 20 to 20.1 min, 2% B from 20.1 to 25 min. Prodrugs were quantified using LC-MS/MS on a Transcend LX2 system (Thermo Fisher, Waltham, Mass.) coupled to an API 4000 (AB Sciex, Framingham, Mass.). As shown in Table 1, both SRM transitions for sodium adduct and base peak from each prodrug were used for LC-MS/MS quantification. Results were consistent with either transition although only data generated with the sodium adduct SRM transitions are shown.

TABLE 1

SRM Transitions Used for Prodrug Quantification by LC-MS/MS

| Prodrug | Transition 1[a] | | Transition 2[b] | |
|---|---|---|---|---|
| | Q1[a] | Q3[a] | Q1[b] | Q3[b] |
| 1 | 1418.6 | 1022.7 | 982.6 | 228.1 |
| 2 | 1392.7 | 996.7 | 956.5 | 342.1 |
| 3 | 1362.7 | 966.6 | 926.5 | 312.3 |
| 4 | — | — | 1255.5 | 451.0 |

SRM transitions used to quantify prodrug-sodium adducts[a] or base peaks[b].

Synthesis of $N^γ$-(9-fluorenyloxycarbonyl)-aminobutyric Acid (Fmoc-GABA)

To a solution of GABA (2.00 g, 19.4 mmol, in 14 mL 10% $NaHCO_3$), Fmoc-OSu (4 g, 11.7 mmol, in 40 mL ACN) was added drop-wise over a period of 2 h at room temperature. The mixture was allowed to stir at room temperature for an additional hour. ACN was removed under reduced pressure and the aqueous layer acidified to pH 1 with 10% HCl. The precipitate was washed with two 20 mL portions of water, 20 mL ethyl acetate and dried under reduced pressure. Fmoc-GABA was obtained as a white solid in 73% yield (2.8 g).

$^1H$ NMR (DMSO-d6, 400 MHz): δ 7.89 (d, 2H, J=7.4 Hz), 7.44 (d, 2H, J=7.2 Hz), 7.42 (t, 2H, J=7.5 Hz), 7.35 (s, 1H), 7.33 (t, 2H, J=7.0 Hz), 4.30 (d, 2H, J=7 Hz), 4.21 (t, 1H, J=6.7 Hz), 3.01 (q, 2H, J=5.6 Hz), 2.20 (t, 2H, J=7.3 Hz), 1.63 (q, 2H, J=7.1 Hz); $^{13}C$ NMR (DMSO-d6, 100 MHz): δ 142.6, 139.4, 137.4, 128.9, 127.2, 124.2, 121.3, 120.0, 109.6, 77.5, 61.8, 51.1, 31.6; MS (ESI+): m/z (intensity), 325.8 ([M+H]+, 100%).

Loading of Fmoc-GABA on 2-chloro-trityl Chloride Resin

Fmoc-GABA (1.2 g, 3.6 mmol) was loaded onto 2-chlorotrityl chloride resin (1 g, 1.7 mmol) in 10 mL of anhydrous DCM/NMP (9:1) in the presence of 4 eq. DIEA at room temperature for 3 h. The loading levels were determined to be 0.48 mmol/g resin by Fmoc-deprotection with 20% piperidine and UV analysis (A290). The unreacted 2-chlorotrityl chloride on the resin was end-capped with 2 mL of methanol/DIEA (9:1) in 10 mL of anhydrous DCM under nitrogen for 60 min at room temperature, and the resin was ready for further coupling after 20% piperidine de-protection.

Synthesis of Prodrug 2 (Glutaryl-Ser-Ala-Ser-Chg-Gln-Ser-Leu-Dox)

Fm-Glutaryl-Ser-Ala-Ser-Chg-Gln-Ser-Leu-OH (SEQ ID NO: 2) was prepared using standard automated peptide synthesis procedures. Fm-glutaryl-Ser-Ala-Ser-Chg-Gln-Ser-Leu-OH (SEQ ID NO: 2) (88 mg, 0.086 mmol) and doxorubicin (25 mg, 0.043 mmol) were dissolved in 2 mL anhydrous DMF in the presence of 2 eq. DIEA. PyBOP (54 mg, 0.10 mmol) was added, and the mixture stirred at room temperature under nitrogen atmosphere for 2 h. Same-pot removal of the fluorenylmethyl-protecting group was achieved with the addition of 200 μL of DEA (10%). Trituration from DMF with 20 mL of ACN and HPLC purification (10 mM ammonium acetate/ACN) afforded the final peptide conjugate in 34% yield (20 mg). Glutaryl-Ser-Ala-Ser-Chg-Gln-Ser-Leu-Dox (SEQ ID NO: 1); HRMS (ESI+): m/z calc'd for $C_{63}H_{88}N_9O_{25}$: $[M+H]^+$=1370.5891, found: 1370.5920.

Synthesis of $N^\gamma$-t-butyloxycarbonyl-aminobutyric Acid (Boc-GABA)

GABA (1.0 g, 9.8 mmol) was dissolved in 24 mL of a 6% $NaHCO_3$ solution at 0° C. A pre-cooled solution of Boc-anhydride (15 mmol in 10 mL dioxane) was added slowly and the mixture stirred at 0° C. for 1 h, then overnight at room temperature. After removing dioxane under reduced pressure, the aqueous mixture was acidified to pH 1 with 1 N sodium bisulfate and extracted with 50 mL ethyl acetate three times. The combined organic layer was washed with 10 mL water, brine and dried over sodium sulfate. Ethyl acetate was removed under reduced pressure and the product collected as a white solid in 84% yield (1.7 g).
$^1$H NMR ($CDCl_3$, 400 MHz): δ 3.21 (m, 2H), 2.42 (t, 2H, J=7.2 Hz), 1.84 (q, 2H, $J_1$=7.0 Hz, $J_2$=6.4 Hz), 1.46 (s, 9H); $^{13}$C NMR ($CDCl_3$, 100 MHz): δ 166.7, 141.3, 125.0, 120.1, 67.8, 46.6, 40.8, MS (ESI+): m/z (intensity), 203.7 ([M+H]+, 45%), 406.8 ([2M+H]+, 74%), 306.8 ([2M+H-Boc]+, 100%).

Synthesis of fluorenylmethyl $N^\gamma$-t-butyloxycarbonyl-aminobutyrate (Boc-GABA-Fm)

Boc-GABA (1.0 g, 9.8 mmol) was pre-activated with CDI (1.6 g, 9.8 mmol) in 2 mL of anhydrous DCM at room temperature under nitrogen atmosphere for 1 h. Fluorenylmethanol (1.3 g, 6.5 mmol) was added and the reaction carried out at room temperature under nitrogen atmosphere for 4 h. The mixture was diluted to 20 mL with DCM, washed sequentially with 20 mL 5% $NaHCO_3$, brine and dried over sodium sulfate. After removing DCM under reduced pressure, the product was collected as an off-white solid in 95% yield (1.2 g). Removal of the Boc-protecting group was carried out with 50% TFA/DCM at room temperature in 30 min. All solvents were removed under a gentle nitrogen stream; the crude product obtained after repeated 20-mL hexane washes (5×) was ready to be used for the next step.
$^1$H NMR ($CDCl_3$, 400 MHz): δ 7.80 (d, 2H, J=8.0 Hz), 7.61 (d, 2H, J=7.4 Hz), 7.44 (t, 2H, J=7.3 Hz), 7.35 (t, 2H, J=7.9 Hz), 4.56 (s, 1H), 4.45 (d, 2H, J=6.7 Hz), 4.24 (t, 1H, J=7.3 Hz), 3.13 (m, 2H), 2.43 (t, 2H, J=7.3 Hz), 1.81 (q, 2H, J=6.8 Hz), 1.46 (s, 9H); $^{13}$C NMR ($CDCl_3$, 100 MHz): δ 143.8, 141.3, 127.8, 127.1, 125.0, 120.0, 66.2, 46.9, 38.4, 31.5, 28.4, 25.3, MS (ESI+): m/z (intensity), 381.7 ([M+H]+, 10%), 282.0 ([M+H-Boc], 100%).

Synthesis of t-BuO-mGly

Malonic acid (5.0 g, 48 mmol) and t-BuOH (1.8 mL, 19 mmol) were dissolved in 150 mL of ACN at room temperature under nitrogen. EDC (9.2 g, 48 mmol) was added and the reaction conducted at room temperature under nitrogen for 30 min. ACN was removed under reduced pressure and the residue dissolved in 200 mL of ether. The product was back-extracted with two 50-mL portions of saturated $NaHCO_3$, and the combined aqueous layer acidified to pH 2 with 1 N sodium bisulfate. Finally, the product was extracted with three 200-mL portions of DCM which were combined and washed with water, brine and dried over sodium sulfate. DCM was removed under reduced pressure and the product obtained as a white solid in 76% yield (2.3 g).
$^1$H NMR ($CDCl_3$, 400 MHz): δ 3.28 (s, 2H), 1.42 (s, 9H); $^{13}$C NMR ($CDCl_3$, 100 MHz): δ 168.5, 162.1, 83.5, 39.7, 27.9, 27.8, 25.6.

Synthesis of t-BuO-mGly-OSu

To a solution (7 mL, ACN) of t-BuO-mGly (2.3 g, 15 mmol) and HOSu (1.7 g, 15 mmol) was added EDC (3.1 g, 16 mmol), and the mixture stirred at room temperature under nitrogen atmosphere for 1 h. ACN was removed under reduced pressure and the residue dissolved in 200 mL of DCM. The organic layer was washed with 50 mL water (2×), brine and dried over sodium sulfate. DCM was removed under reduced pressure and the crude product collected as a white solid in 84% yield (3.1 g).

Synthesis of Fm-GABA←mGly

A solution of t-BuO-mGly-OSu (1.8 g, 6.9 mmol) and GABA-Fm (2.0 g, 6.9 mmol) was prepared in 25 mL of anhydrous DCM in the presence of DIEA (1.2 mL, 6.9 mmol) and stirred at room temperature under nitrogen atmosphere for 1 h. The reaction mixture was diluted to 40 mL with DCM, washed with 10 mL water (2×), brine and dried over sodium sulfate. DCM was removed under reduced pressure and the crude mixture purified by FCC to afford the final product in 64% yield (1.9 g). Removal of the t-butyl-protecting group was achieved with 50% TFA/DCM to afford 1.7 g of the free acid which was carried forward to the next step without further purification.

Synthesis of Fm-GABA←-mGly-Ala-Ser-Chg-Gln-Ser-Leu-OH (8)

The Fm-GABA←mGly-OSu ester was freshly prepared and coupled to the amino end of H-Ala-Ser-Chg-Gln-Ser- Leu-OH (SEQ ID NO: 3). The peptide intermediate was obtained using standard automated peptide synthesis procedures. To prepare the OSu ester, Fm-GABA←mGly (320 mg, 0.87 mmol) and HOSu (100 mg, 0.87 mmol) were dissolved in 6 mL of ACN. EDC (420 mg, 2.2 mmol) was added and the mixture stirred at room temperature under nitrogen for 1 h. ACN was removed, the residue dissolved in 40 mL of DCM, washed with 10 mL water (3×), brine and dried over sodium sulfate. The crude OSu ester (220 mg, 0.48 mmol) was directly coupled (<1 min) to H-Ala-Ser-Chg-Gln-Ser-Leu-OH (SEQ ID NO: 3) (310 mg, 0.48 mmol) in the presence of 1 eq. DIEA in 1 mL ACN/NMP (1:2). Trituration with 30 mL of ice-cold ether afforded 310 mg of the crude peptide which was used for the next step without further purification.

Synthesis of Prodrug 3 (GABA←mGly-Ala-Ser-Chg-Gln-Ser-Leu-Dox)

Fm-GABA←mGly-Ala-Ser-Chg-Gln-Ser-Leu-OH (96 mg, 0.096 mmol) and doxorubicin (28 mg, 0.048 mmol) were dissolved in the presence of 2 eq. DIEA in 2 mL anhydrous DMF. PyBOP (60 mg, 0.12 mmol) was added and the mixture stirred at room temperature under nitrogen atmosphere for 2 h. Same-pot removal of the fluorenylmethyl-protecting group was achieved with the addition of 200 µL of DEA (10%). Trituration from DMF with 20 mL of ACN and HPLC purification (10 mM ammonium acetate/ACN) afforded the final peptide conjugate in 28% yield (18 mg). GABA←mGly-Ala-Ser-Chg-Gln-Ser-Leu-Dox; HRMS (ESI+): m/z calc'd for $C_{62}H_{86}N_9O_{24}$: $[M+H]^+=1340.5786$, found: 1340.5817.

Synthesis of Methyl 3-((1,3-dioxoisoindolin-2-yl)oxy)-2,2-dimethylpropanoate (12)

A solution of DIAD (2.8 mL, 15 mmol) prepared in 5 mL anhydrous THF) was slowly added to a stirred mixture of methyl 3-hydroxy-2,2-dimethylpropanoate (2.0 g, 15 mmol), triphenylphosphine (4.4 g, 17 mmol) and N-hydroxyphthalimide (2.7 g, 317 mmol) prepared in 80 mL anhydrous THF at 0° C. After stirring the mixture at room temperature under a nitrogen atmosphere for 24 h, THF was removed under reduced pressure and the residue re-dissolved in 40 mL of ethyl acetate. The ethyl acetate mixture was washed with water (10 mL) three times, brine and dry-loaded onto a 80-g silica column. The final product was obtained in 57% yield (2.4 g) as a white solid after FCC purification from hexane/ethyl acetate.

$^1$H NMR (CDCl$_3$, 400 MHz): δ 7.84 (m, 2H), 7.76 (s, 2H), 4.28 (s, 2H), 3.77 (s, 3H), 1.40 (s, 6H); $^{13}$C NMR (CDCl$_3$, 100 MHz): δ 175.7, 163.1, 136.0, 134.4, 129.0, 123.4, 83.7, 52.2, 43.1, 22.2, MS (ESI+): m/z (intensity), 278.2 ([M+H]+, 100%).

Synthesis of Methyl 3-(aminooxy)-2,2-dimethylpropanoate (13)

To a solution of methyl 3-((1,3-dioxoisoindolin-2-yl)oxy)-2,2-dimethylpropanoate (160 mg, 0.57 mmol) prepared in 10 mL of anhydrous diethyl ether was added 73 µL (2.3 mmol) of 98% anhydrous hydrazine, and the mixture stirred at room temperature under a nitrogen atmosphere for 2 h. The mixture was filtered and the filtrate concentrated to generate 75 mg of crude methyl 3-(aminooxy)-2,2-dimethylpropanoate (white solid) which was used for the next step without further purification.

Synthesis of N$^\alpha$-allyloxycarbonyl-N$^\delta$-trityl-L-glutamine (Alloc-Gln(Trt)-OH, 15)

A solution of allylchloroformate prepared in 20 mL of ACN was slowly added to a stirred suspension of H-Gln(Trt)-OH (390 mg, 1.0 mmol) in 10 mL of 10% K$_2$CO$_3$ at room temperature over a period of 10 min. After stirring the mixture for an additional 10 min at room temperature, the organic layer was collected and ACN removed under reduced pressure. Toluene (10 mL, 3×) was added to the residue and the solvent removed under reduced to pressure to give Alloc-Gln(Trt)-OH as a white solid in 95% yield (450 mg).

$^1$H NMR (CDCl$_3$, 400 MHz): δ 7.27 (m, 15H), 5.95 (m, 2H), 5.32 (ddd, 1H, J$_1$=9.2 Hz, J$_2$=1.6 Hz, J$_3$=0.72 Hz), 5.19 (ddd, 1H, J$_1$=5.1 Hz, J$_2$=1.5 Hz, J$_3$=0.59 Hz), 4.53 (d, 2H, J=2.4 Hz), 4.06 (t, 1H, J=6.5 Hz), 2.39 (t, 2H, J=8.3 Hz), 2.00 (m, 2H); $^{13}$C NMR (CDCl$_3$, 100 MHz): δ 178.6, 175.1, 157.7, 146.1, 134.5, 130.1, 128.7, 127.7, 117.5 71.8, 66.6, 57.2, 34.4, 30.9, MS (ESI+): m/z (intensity), 473.4 ([M+H]+, 100%).

Synthesis of Alloc-Gln(Trt)-OSu (16)

To a stirred solution (20 mL of ACN) of Alloc-Gln(Trt)-OH (150 mg, 0.32 mmol) and HOSu (44 mg, 0.38 mmol) was added EDC (240 mg, 1.3 mmol), and the mixture stirred at room temperature under nitrogen atmosphere for 2 h. ACN was removed under reduced pressure and the residue dissolved in 40 mL of DCM. The organic layer was washed with 10 mL water (2×), brine and dried over sodium sulfate. DCM was removed under reduced pressure and the crude ester collected as a white solid in quantitative yield (190 mg).

Synthesis of Methyl (S)-2,2-dimethyl-6,9-dioxo-7-(3-oxo-3-(tritylamino)propyl)-4,10-dioxa-5,8-diazatridec-12-enoate (Alloc-Gln(Trt)-NH—O—CH$_2$—C(Me)$_2$COOMe, 17)

To a stirred solution (80 mL of ACN) of Alloc-Gln(Trt)-OH (489 mg, 1.0 mmol) and HOSu (253 mg, 2.2 mmol) was added EDC (768 mg, 4.0 mmol) and the mixture stirred at room temperature under nitrogen atmosphere for 2 h. In parallel, methyl 3-((1,3-dioxoisoindolin-2-yl)oxy)-2,2-dimethylpropanoate (834 mg, 3.0 mmol) was de-protected with anhydrous hydrazine (383 µL, 12.0 mmol) as previously described, the resulting crude solid dissolved in 8 mL of anhydrous DCM, and directly added to the Alloc-Gln(Trt)-OSu ester solution. The mixture was stirred at room temperature under nitrogen atmosphere for 24 h, ACN removed under reduced pressure and the DMF solution triturated with 10 volumes (80 mL) of ice-cold water. After centrifugation at 3000 RPM for 15 min, the white precipitate was collected and dry-loaded on a 24-g silica column and purified from DCM/ACN. The final product was obtained as a white solid in 86% yield (520 mg).

$^1$H NMR (CD$_3$OD, 400 MHz): δ 7.27 (m, 15H), 5.95 (m, 1H), 5.32 (ddd, 1H, J$_1$=9.1 Hz, J$_2$=1.6 Hz, J$_3$=0.73 Hz), 5.19 (ddd, 1H, J$_1$=5.1 Hz, J$_2$=1.5 Hz, J$_3$=0.60 Hz), 4.56 (d, 2H, J=5.1 Hz), 3.93 (m, 3H), 3.69 (s, 3H), 2.45 (m, 2H), 1.91 (m, 2H); $^{13}$C NMR (CD$_3$OD, 100 MHz): δ 177.9, 174.1, 171.1, 158.2, 146.0, 134.3, 130.0, 128.7, 127.8, 117.8, 83.4, 71.7, 66.7, 53.8, 52.6, 44.1, 33.7, 29.0, 22.7, MS (ESI+): m/z (intensity), 602.4 ([M+H]+, 100%).

Syntheses of (S)-7-(3-amino-3-oxopropyl)-2,2-dimethyl-6,9-dioxo-4,10-dioxa-5,8-diazatridec-12-enoic Acid (Alloc-Gln-NH—O—CH$_2$—C(Me)$_2$COOH, 18) and its Sodium Salt To a THF solution (36 mL) of Alloc-Gln(Trt)-NHO—CH$_2$—C(Me)$_2$COOMe (524 mg, 0.87 mmol) was added 4 mL of a 1 N NaOH solution, and the mixture stirred at room temperature for 24 h. Solvents were removed under reduced pressure, the residue redissolved in 40 mL of DCM and washed with 10 mL of H$_2$O three times and 10 mL of brine. After drying the organic layer on sodium sulfate, solvents were removed to a white solid. The residue was allowed to stir in 2 mL of 95% TFA/DCM at 0° C. for 5 min. Following trituration with 10 mL of ice-cold water, the mixture was lyophilized. The sodium salt of Alloc-Gln-NHO—CH$_2$—C(Me)$_2$COOH was obtained by dissolving the lyophilisate in 5 mL of ACN followed by neutralization to pH 7 (slow addition of a NaHCO$_3$ (2 eq.) solution at 0° ° C.) and lyophilizing the mixture. The sodium salt was used for the next step without further workup.

Synthesis of 14-bromodaunorubicin HCl (20)

Trimethylorthoformate (100 μL) was added to a solution of daunomycin HCl (100 mg, 0.18 mmol) prepared in 6 mL of Dioxane/MeOH (2:1) and the mixture stirred at room temperature for 20 min. A Br$_2$/CHCl$_3$ (0.22 mmol in 370 μL) solution was added dropwise and the mixture stirred at room temperature for an additional 40 min. Precipitation with 100 mL of ice-cold ether, followed by an ether wash (100 mL) and filtration afforded a red solid. The final product was obtained in 89% yield (102 mg) by recrystallization from 5 mL acetone/ether (1:1).

$^1$H NMR (DMSO-d6, 400 MHz) δ 13.92 (s, 1H), 13.13 (s, 1H), 7.81 (m, 2H), 7.75 (s, 2H), 7.56 (dd, 1H, J$_1$=2.1, J$_2$=8.2 Hz), 5.22 (m, 1H), 4.85 (m, 1H), 4.12 (q, 1H, J=7.7 Hz), 3.90 (s, 5H), 3.52 (s, 1H), 3.31 (m, 1H), 3.06 (d, 1H, J=19.1), 2.83 (d, 1H, J=33.1 Hz), 2.43 (q, 2H, J=2.0 Hz), 2.21 (d, 1H, J=14.3), 1.89 (dd, 1H, J$_1$=3.9, J$_2$=12.7 Hz), 1.68 (d, 1H, J=11.6 Hz)), 1.18 (d, 3H, J=5.7 Hz); $^{13}$C NMR (DMSO-d6, 100 MHz): δ 213.7, 205.6, 186.4, 186.3, 160.7, 156.0, 154.4, 154.3, 136.2, 135.1, 134.6, 133.8, 119.9, 119.7, 119.0, 110.7, 99.1, 96.5, 89.4, 75.4, 69.7, 66.1, 56.6, 54.0, 40.1, 39.7, 34.1, 18.5, 16.7, MS (ESI+): m/z (intensity), 606.3 ([M+H]+, 100%).

Synthesis of 2-((2S,4S)-4-(((2R,4S,5S,6S)-4-((((9H-fluoren-9-yl)methoxy)carbonyl)amino)-5-hydroxy-6-methyltetrahydro-2H-pyran-2-yl)oxy)-2,5,12-trihydroxy-7-methoxy-6,11-dioxo-1,2,3,4,6,11-hexahydrotetracen-2-yl)-2-oxoethyl (S)-7-(3-amino-3-oxopropyl)-2,2-dimethyl-6,9-dioxo-4,10-dioxa-5,8-diazatridec-12-enoate (Alloc-Gln-NH—O—CH$_2$—C(Me)$_2$C(O)-14-O-(Fmoc-Dox), 10a)

Alloc-Gln-NHO—CH$_2$—C(Me)$_2$COOH (297 mg, 0.86 mmol) was converted to its sodium salt as previously described, added to a 10-mL acetone solution of 14-daunorubicinicin HCl (50 mg, 0.078 mmol) in the presence of 3 Å molecular sieves, and the mixture stirred at room temperature for 48 h. After adding 10 mL of methanol, the mixture was centrifuged at 3000 rpm for 15 min. The supernatant was collected, dried in vaccuo and reconstituted in 1 mL of anhydrous ACN in the presence of DIEA (2 eq.). Protection the aminoglycoside was carried out with the addition of Fmoc-Osu (27 mg, 0.08 mmol) and stirring the mixture for 30 min at room temperature. Two-step FCC purification from DCM/ACN; DCM/(20% MeOH/DCM) afforded 31 mg of crude (36% yield, >90% pure) Fmoc-Dox-PAD-Gln-Alloc as a dark orange solid (m/z=1093.3). Alloc-deprotection was performed with tetrakis(triphenylphosphine)palladium(0) (3 mg, 0.0028 mmol)/dimedone (27 mg, 0.19 mmol) in 2 mL of anhydrous THF at room temperature for 2 h. After removing THF, the amine was redissolved in 1 mL of anhydrous DMF and triturated with 20 mL of ice-cold ether. The pellet was collected after centrifugation at 3000 rpm, and the titration step was repeated two additional times to remove residual catalyst. The crude orange solid (compound 10a) was used for the next step without further purification.

$^1$H NMR (DMSO-d6, 400 MHz): δ 11.31 (s, 2H), 7.73 (m, 2H), 7.63 (m, 2H), 7.40 (m, 2H), 7.32 (m, 2H), 6.76 (m, 1H), 5.64 (s, 1H), 5.22 (m, 3H), 4.96 (s, 1H), 4.52 (d, 2H, J=5.7 Hz), 4.40 (m, 1H), 4.00 (s, 3H), 3.77 (s, 2H), 3.52 (m, 1H), 3.46 (m, 1H), 2.86 (d, 1H, J=17.9 Hz), 2.09 (m, 8H), 1.27 (s, 6H), 1.11 (d, 3H, J=2.8 Hz); $^{13}$C NMR (DMSO-d6, 100 MHz): δ 210.2, 186.4 176.4, 173.4, 172.7, 167.7, 156.1, 155.8, 140.6, 133.5, 133.4, 127.5, 127.0, 125.2, 120.2, 117.1, 75.2, 65.7, 64.1, 56.5, 42.4, 41.9, 40.1, 39.9, 39.7, 38.9, 31.3, 25.2, 23.2, 22.2, 22.0, MS (ESI+): m/z (intensity), 1093.4 ([M+H]+, 100%).

Synthesis of Benzyl 3-((1,3-dioxoisoindolin-2-yl)oxy)-2,2-dimethylpropanoate A solution of diisopropylazodicarboxylate (DIAD, 0.52 mL, 2.8 mmol) prepared in 2 mL anhydrous THF) was slowly added to a stirred mixture of benzyl 3-hydroxy-2,2-dimethylpropanoate (590 mg, 2.8 mmol), triphenylphosphine (820 mg, 3.1 mmol) and N-hydroxyphthalimide (510 mg, 3.1 mmol) prepared in 20 mL anhydrous THF at 0° C. After stirring the mixture at room temperature under a nitrogen atmosphere for 24 h, THF was removed under reduced pressure and the residue re-dissolved in 40 mL of ethyl acetate. The ethyl acetate mixture was washed with water (10 mL) three times, brine and dry-loaded onto a 40-g silica column. The final product was obtained in 73% yield (730 mg) as a white solid after FCC purification (hexane/ethyl acetate).

$^1$H NMR (CDCl$_3$, 400 MHz): δ7.84 (m, 2H), 7.76 (s, 2H), 7.39 (m, 5H), 5.19 (s, 2H), 4.32 (s, 2H), 1.42 (s, 6H); $^{13}$C NMR (CDCl3, 100 MHz): δ 175.0, 163.1, 136.0, 134.4, 129.0, 128.5, 128.1, 123.5, 83.6, 66.7, 43.2, 22.2, MS (ESI+): m/z (intensity), 354.4 ([M+H]+, 100%).

Synthesis of 3-((1,3-dioxoisoindolin-2-yl)oxy)-2,2-dimethylpropanoic Acid

Hydrogenation of benzyl 3-((1,3-dioxoisoindolin-2-yl)oxy)-2,2-dimethylpropanoate (570 mg, 1.6 mmol) was accomplished in the presence of 10% Pd—C in 20 mL de-aerated methanol at room temperature for 5 h. The mixture was filtered through a layer of celite and concentrated to a crude oil (345 mg, 82%), which was used for the next step without further purification.

Synthesis of 3-(aminooxy)-2,2-dimethylpropanoic acid (NH$_2$—O—CH$_2$—C(Me)$_2$COOH, 24)

To a solution of 3-((1,3-dioxoisoindolin-2-yl)oxy)-2,2-dimethylpropanoic acid (150 mg, 0.57 mmol) prepared in 10 mL of anhydrous diethyl ether was added 36 μL (1.1 mmol) of 98% anhydrous hydrazine, and the mixture stirred at room temperature under a nitrogen atmosphere for 2 h. The mixture was filtered and the filtrate concentrated to generate 78 mg of crude NH$_2$—O—CH$_2$—C(Me)$_2$COOH (white solid) which was used for the next step without further purification.

Synthesis of Fmoc-Gln-OSu (26)

To a stirred solution (20 mL of ACN) of Fmoc-Gln(Trt)-OH (611 mg, 1.0 mmol) and HOSu (150 mg, 1.3 mmol) was added EDC (290 mg, 1.5 mmol), and the mixture stirred at room temperature under nitrogen atmosphere for 2 h. ACN was removed under reduced pressure and the residue dissolved in 40 mL of DCM. The organic layer was washed with 10 mL water (2×), brine and dried over sodium sulfate. DCM was removed under reduced pressure, and the residue treated with 10 mL of 95% TFA at room temperature for 5 min. FCC purification (20% MeOH/DCM) afforded 471 mg of crude Fmoc-Gln-Osu (26) as a white solid.

Synthesis of (S)-5-(3-amino-3-oxopropyl)-1-(9H-fluoren-9-yl)-10,10-dimethyl-3,6-dioxo-2,8-dioxa-4,7-diazaundecan-11-oic Acid (Fmoc-Gln-NH—O—CH$_2$—C(Me)$_2$COOH, 27)

Crude NH$_2$—O—CH$_2$—C(Me)$_2$COOH (450 mg, 3.3 mmol) and Fmoc-Gln-OSu (466 mg, 1.0 mmol) were dissolved in 5 mL of anhydrous DMF and the mixture stirred at room temperature under nitrogen atmosphere for 24 h. DMF was removed under reduced pressure and the residue dry-loaded onto a 40 g silica column. FCC purification (DCM/ACN/(20% MeOH/DCM)) afforded Fmoc-Gln-NHO—CH$_2$—C(Me)$_2$COOH as a white solid in 66% yield (321 mg).

$^1$H NMR (CD$_3$OD, 400 MHz): δ 7.81 (d, 2H, J=7.61 Hz), 7.68 (d, 2H, J=5.71 Hz), 7.40 (t, 2H, J=6.66 Hz), 7.33 (t, 2H, J=7.61 Hz), 4.39 (d, 2H, J=3.76 Hz), 4.23 (t, 1H, J=6.88 Hz), 3.94 (s, 2H), 2.29 (m, 2H), 2.06 (m, 2H), 1.26 (s, 6H); $^{13}$C NMR (CD$_3$OD, 100 MHz): δ 145.3, 145.2, 142.6, 134.0, 128.8, 128.2, 126.6, 126.2, 120.9, 83.5, 68.0, 53.8, 49.6, 43.8, 32.4, 28.9, 22.9, MS (ESI+): m/z (intensity), 484.3 ([M+H]+, 100%).

Synthesis of 2-((2S,4S)-4-(((2R,4S,5S,6S)-4-(((allyloxy)carbonyl)amino)-5-hydroxy-6-methyltetrahydro-2H-pyran-2-yl)oxy)-2,5,12-trihydroxy-7-methoxy-6,11-dioxo-1,2,3,4,6,11-hexahydrotetracen-2-yl)-2-oxoethyl 3-(((S)-2,5-diamino-5-oxopentanamido)oxy)-2,2-dimethylpropanoate (Fmoc-Gln-NH—O—CH$_2$—C(Me)$_2$C(O)-14-O-(Alloc-Dox), 10b)

Fmoc-Gln-NH—O—CH$_2$—C(Me)$_2$COOH (335 mg, 0.66 mmol) was converted to its sodium salt as previously described, added to a 10-mL acetone solution of 14-daunorubicin HCl (53 mg, 0.083 mmol) in the presence of 3 Å molecular sieves, and the mixture stirred at room temperature for 48 h. After adding 10 mL of methanol, the mixture was centrifuged at 3000 rpm for 15 min. The supernatant was collected, dried in vaccuo and reconstituted in 4 mL of anhydrous ACN. Protection the aminoglycoside was carried out with the addition of Alloc-OSu (33 mg, 0.17 mmol) in the presence of 2 equivalents of NaHCO$_3$ (suspension) and stirring the mixture for 1 h at room temperature. Two-step FCC purification from DCM/ACN; DCM/(20% MeOH/DCM) afforded the title compound in 40% yield (40 mg, greater than 90% pure by LC-UV). Fmoc-deprotection of Fmoc-Gln-NH—O—CH$_2$—C(Me)$_2$C(O)-14-O-(Alloc-Dox) was performed with 1% DBU in 1 mL of anhydrous DMF at room temperature in 10 min. Trituration with 10 mL of ice-cold ether followed by centrifugation at 3000 rpm afforded a dark orange solid which was purified by HPLC (10 mM ammonium acetate/ACN) to afford 17 mg of crude H-Gln-NHO—CH$_2$—C(Me)$_2$C(O)-14-O-(Alloc-Dox) (compound 10b).

$^1$H NMR (DMSO-d6, 400 MHz): δ 11.32 (s, 2H), 7.90 (m, 2H), 7.69 (m, 2H), 7.41 (m, 2H), 7.30 (m, 3H), 5.61 (s, 1H), 5.24 (m, 3H), 4.94 (s, 1H), 4.54 (d, 2H, J=5.4 Hz), 4.46 (m, 1H), 3.99 (s, 3H), 3.87 (s, 2H), 3.81 (m, 1H), 3.64 (m, 1H), 2.96 (d, 1H, J=18.5 Hz), 2.10 (m, 8H), 1.27 (s, 6H), 1.11 (d, 3H, J=2.9 Hz); $^{13}$C NMR (DMSO-d6, 100 MHz): δ 210.0, 202.0, 174.5, 173.4, 172.7, 156.0, 154.5, 143.7, 140.6, 133.6, 127.6, 127.0, 125.3, 120.0, 116.8, 75.2, 66.7, 65.7, 64.1, 56.5, 46.6, 42.4, 40.1, 39.9, 39.7, 38.9, 31.2, 25.2, 22.1, 22.0, MS (ESI+): m/z (intensity), 1093.2 ([M+H]+, 100%).

Synthesis of Prodrug 4 (GABA←mGly-Ala-Ser-Chg-Gln-NH—O—CH$_2$—C(Me)$_2$C(O)-14-O-Dox)

Fm-GABA←mGly-Ala-Ser-Chg-OH (7.6 mg, 0.011 mmol) and H-Gln-NHO—CH$_2$—C(Me)$_2$C(O)-14-O-(Alloc-Dox) (5 mg, 0.0057 mmol) were dissolved in 300 μL of anhydrous DMF in the presence of DIEA (3 eq.) and the mixture allowed to stir under nitrogen at 0° C. for 10 min. A solution of HATU (4.1 mg, 0.011 mmol, 200 μL in anhydrous DMF) was added dropwise, and the mixture stirred at 0° C. for 1 h to warm-up to room temperature in 1 h. Trituration with 5 mL of ice-cold water, followed by centrifugation afforded a dark orange solid which was dissolved in 5 mL of methanol and dried over sodium sulfate. After removing methanol under reduced pressure, the residue was dissolved in 500 μL of anhydrous THF in the presence of dimedone (11 mg, 0.08 mmol), and catalytic tetrakis(triphenylphosphine)palladium(0) added. The mixture was stirred at room temperature for 1 h to allow complete deprotection of the Alloc-protecting group. Addition of 5 mL of ice-cold ether followed by centrifugation at 10,000 rpm (repeated 3 three times) gave an orange solid which was re-dissolved in 500 μL of anhydrous DMF. Fm-deprotection was performed with 2% DBU at room temperature in 10 min. The mixture was triturated with ice-cold ether as previously described, and the final peptide conjugate obtained in 18% yield (1.3 mg) after HLPC purification. GABA←mGly-Ala-Ser-Chg-Gln-NHO—CH$_2$—C(Me)$_2$C(O)-14-O-Dox; HRMS (ESI+): m/z calc'd for C$_{58}$H$_{79}$N$_8$O$_{23}$: [M+H]$^+$=1255.5258, found: 1255.5254.

Synthesis of Fm-GABA←mGly-Ala-Ser-Chg-OH (7a)

The Fm-GABA←mGly-OSu ester was freshly prepared as previously described and coupled to the amino end of H-Ala-Ser-Chg-OH. The tri-peptide was generated using standard automated peptide synthesis procedures. The OSu ester (410 mg, 0.87 mmol) was directly coupled (within 1 min) to H-Ala-Ser-Chg-OH (230 mg, 0.73 mmol) in 1 mL ACN/NMP (1:2) in the presence of 1 eq. DIEA. After FCC purification, the final peptide was obtained in 56% yield (270 mg).

Alternate Synthesis

Fm-GABA←mGly-OSu ester was freshly prepared as previously described from Fm-GABA←mGly (210 mg, 0.57 mmol), HOSu (66 mg, 0.57 mmol) and EDC (130 mg, 0.68 mmol) in 3 mL of anhydrous DCM at room temperature under a nitrogen atmosphere for 1 h. The reaction mixture was diluted to a 10-mL solution in DCM/DMF (9:1), added to the amino end of H-Ala-Ser-Chg-resin (0.5 g, 0.27 mmol) and the mixture stirred at room temperature under nitrogen atmosphere for 24 h; the resin-bound tri-peptide was generated on Wang resin using standard automated peptide synthesis procedures. The final peptide was cleaved off the resin with three 10-mL portions of 95% TFA/DCM. TFA was azeotroped off with 30-mL portions (5×) and the final peptide (180 mg) was ready to be used for the next step without further purification.

Prodrug 4 (GABA←mGly-Ala-Ser-Chg-Gln-NH—O—CH$_2$—C(Me)$_2$C(O)-14-O-Dox) was prepared by coupling Fm-GABA←mGly-Ala-Ser-Chg to Gln-NH—O—CH$_2$—C(Me)$_2$C(O)-14-O-Dox-NH-Alloc (10a). Preparation of Fm-GABA←mGly-Ala-Ser-Chg (7) and Fm-GABA←mGly-Ala-Ser-Chg-Gln-Ser (8) could not be achieved following standard automated peptide synthesis methods because coupling of Fm-GABA←mGly to Ala-Ser-Chg-O— resin failed when EDC, HBTU or PyBOP were used to activate the acid. Furthermore, premature removal of the Fm-protecting group was observed under conditions featuring greater than 1 equivalent of DMAP. Instead, Fm-GABA←mGly-OSu was prepared and coupled to H-Ala-Ser-Chg-Gln-Ser (SEQ ID NO: 7) or Ala-Ser-Chg in solution. Additionally, Fm-GABA←mGly-Ala-Ser-Chg could be readily generated by coupling the Fm-GABA←mGly-OSu ester to H-Ala-Ser-Chg-O-resin at room temperature in 48 h.

The 3-aminoxypropionate moiety of prodrug 4 was obtained as follows. Ready access to compound 12 was achieved in greater than 50% yield in a single step starting from either methyl or benzyl 3-hydroxy-2,2-dimethylpropanoate. Using methyl 3-hydroxy-2,2-dimethylpropanoate as a starting point, removal of the phthalimido group with anhydrous hydrazine afforded the methyl ester of the 3-aminoxypropionate intermediate 13 which was subsequently coupled to Alloc-Gln(Trt)-OH via its OSu ester (see FIG. 3). Trityl-protection of the Gln side-chain amide was introduced in earlier steps for convenient UV detection during the FCC purification of compound 15 (see FIG. 3, compounds 14 & 15, step c).

Due to the poor stability of doxorubicin under acidic deprotection and hydrogenation conditions, an orthogonal protection strategy involving an acid- and base-stable protecting group for either the α-amino or C-4 amino group of Gln or doxorubicin, respectively, was necessary. An Fmoc/Alloc orthogonal protection strategy was used so that the Alloc group could be removed with tetrakis(triphenyl-phosphine)palladium(O) in the presence of the allyl scavenger dimedone, and Fmoc deprotected with a non-nucleophilic base such as 1,8-diazabicycloundec-7-ene (DBU). To circumvent the poor solubility of H-Gln(Trt)-OH in most solvents, a 2-phase reaction system (10% K$_2$CO$_3$ and acetonitrile) followed by slow allylchloroformate addition afforded Alloc-Gln(Trt)-OH in excellent yield (95%) and purity. Coupling of compound 13 to Alloc-Gln(Trt)-OH (15) via the OSu ester (16) was carried out in a one-pot procedure in the presence of excess EDC.

A few specific doxorubicin-14-O-esters were prepared by chemoenzymatic methods using *Candida antarctica* lipase (type B); however, the conventional approach for synthesizing doxorubicin-14-O-esters involves a nucleophilic displacement-type esterification of 14-bromodaunorubicin (20) under basic conditions. To access 14-bromodaunorubicin, C-14 bromination was efficiently carried out through ketalization of the carbonyl group at C-13 (FIG. 4).

The hydroxypivalic acid doxorubicin-14-O-ester (22) could be readily synthesized from sodium hydroxypivalate (21) and 14-bromodaunorubicin (20) at 50° C. in dry acetone (FIG. 4) as previously reported for various doxorubicin-14-O-esters generated from aspartic acid derivatives and fatty acids (Rho et al. (2001) *Bull. Korean Chem. Soc.* 22:587-592; Rho et al. (2000) *Bull. Korean Chem. Soc.* 21:774-778; Rho et al. (2002) *Synth. Commun.* 32:1961-1975). Under those conditions, significant aglycone formation also occurred due to in situ generation of HBr. In addition, hydrolysis of 14-bromodaunorubicin to doxorubicin (~10%) was observed leading to a further reduction of the reaction yield to less than 50%. However, nearly quantitative conversion to the hydroxypivalate doxorubicin-14-O-ester was achieved by increasing the solvent volume and adding 3 Å molecular sieves to the reaction mixture to trap HBr.

Convenient access to doxorubicin-14-O-esters 10a and 10b was thus possible through coupling of compound 18 or 27 to 14-bromodaunorubicin (20) at room temperature for 48 h, followed by Alloc- or Fmoc-protection, respectively (FIGS. 3 and 6). The conversion yield of the bromo-substitution steps affording esters 10a and 10b was improved to up to 80% when a minimum of 5 equivalents of the acid was used; nevertheless, longer reaction times led to significant hydrolysis of the esters to doxorubicin (greater than 20%) and overall yields greater than 40% could not be achieved for the protected esters. Additionally, FCC purification of the protected esters was difficult due to their poor solubility. Consequently, the deprotected ester 10b was purified and isolated by HPLC. Finally, prodrug 4 was obtained by coupling GABA←mGly-Ala-Ser-Chg-Gln to ester 10b using HATU.

Figure 2:
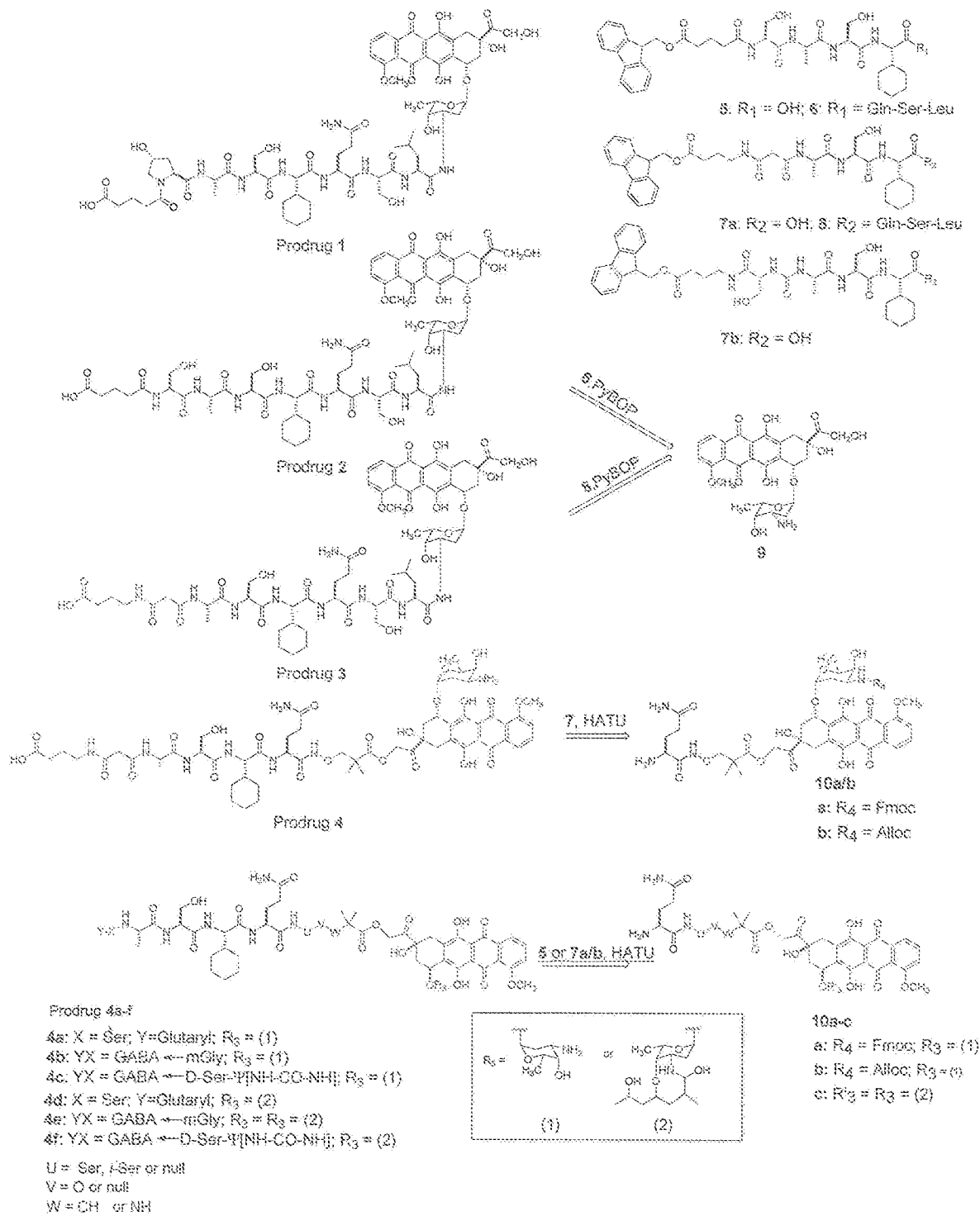
FIG. 2 represents general prodrug synthetic strategy.

Using standard solid-phase peptide synthesis procedures (Barany, G. and Merrifield, The Peptides 2:1 284, Gross and Meienhofer, Eds., Academic Press, New York), prodrugs 1-3 were prepared by first generating the appropriate sequences, which were subsequently coupled to the amino end of Leu-Doxorubicin via PyBOP activation as shown in FIG. 2.

The following non-limiting examples serve to further illustrate the present invention.

VII. EXAMPLES

1. Prodrug Evaluation in PSA- and Non-PSA-Producing Cells

A. Measurement of Peptide Concentration and the PSA Enzyme Assay

For doxorubicin conjugates, peptide solution concentrations were determined by measuring the UV absorbance at 484 and 254 nm (20 μM for doxorubicin and 50 μM for phosphoramide mustard conjugates, respectively) of solutions prepared (based on weight) in water from 10 mM DMSO stock solutions. Using the extinction coefficients of doxorubicin at 484 nm (10,800 M-1·cm-1), peptide concentrations were calculated and adjusted accordingly to prepare 100 μM solutions in 50 mM Tris buffer, pH 8 containing 2 mM CaCl$_2$ and 0.1% Tween 20. The stability of peptide conjugates in 50 mM Tris buffer, pH 8 was determined from 48-h incubations in buffer (FIG. 7). Peptide solutions were prepared in Tris buffer pH 8 at a concentration of 1.11 μM from 1 mM DMSO stock solutions, and warmed up to 37° C. Reactions were initiated at 37° C. with the addition of 5 μL aliquots of a 10 μM solution of human PSA to 45 μL aliquots of the 1.11 μM peptide solutions in eppendorf vials (total volume 50 μL, final PSA concentration 1 μM), and time points recorded over a period of 3 h. Reactions were terminated at 0, 10, 20, 30, 60, 120, 180 and 360 min by quenching 2 μL aliquots of incubates with 20 μL of chilled 50% ACN containing 0.1 μM internal standard (IS) and 0.1% formic acid (FA) pre-added to eppendorf vials. Samples were centrifuged at 3000 RPM for 15 min and the supernatants analyzed by LC-MS/MS in SRM mode as previously described. The fraction of prodrug remaining at each time point was calculated by dividing the prodrug/IS ratio by the 0-h prodrug/IS area ratio and half-life determined from prodrug disappearance rate.

B. Prodrug Stability in Tris Buffer

The stability of doxorubicin peptide conjugates in 50 mM Tris buffer, pH 8 was studied over a period of 48 h. Prodrug disappearance was monitored by LC-MS/MS analysis using selected-reaction monitoring (SRM). As shown in FIG. 7, most prodrugs were ~80% stable in Tris buffer, pH 8 over a period of 24 hours. LC-MS analysis of the buffer incubates revealed that one of the major degradants of doxorubicin conjugates 1-3 was a putative Tris-adduct (confirmed by accurate mass) probably originating from the condensation of trisaminomethane with trace amounts of the terminal aldehyde (tautomerized α-hydroxyketone) of doxorubicin. Another late-eluting degradant with retention time of 17.5 min was detected but could not be identified based on mass spectral data. PSA cleavage of prodrugs 1-4 proceeds through mechanisms affecting the peptide promoiety, which are distinct from the slow degradation observed in buffer.

C. PSA Cleavage Rate and Half-Life Determination

To determine PSA cleavage rates, doxorubicin prodrugs 1-4 were incubated with human PSA over a period of 3 h. Substrate disappearance was monitored by LC-MS/MS analysis using SRM. The percentage of prodrug remaining at any given time point was computed by taking the ratio of its peak area response and that of the 0-h time point. (FIG. 8). Overall, linkage of PSA-cleavable peptides through the aminoglycoside (prodrugs 1-3) or to the C-14 α-hydroxyl (prodrug 4) of doxorubicin both afforded prodrugs that were cleaved at sufficiently fast rates, and some comparable to that of L-377,202.

TABLE 2

Hydrolysis of Doxorubicin Prodrugs by PSA

| Prodrug | PSA peptide linkage site | % of prodrug at 60 min | $t_{1/2}$ (min) |
|---|---|---|---|
| Glutaryl-Hyp-Ala-Ser-Chg-Gln-Ser-Leu-Dox (SEQ ID NO: 4) (1) | Aminoglycoside (reference prodrug) | 13 | 23 |
| Glutaryl-Ser-Ala-Ser-Chg-Gln-Ser-Leu-Dox (SEQ ID NO: 1) (2) | Aminoglycoside (reference prodrug) | 12 | 22 |
| GABA←mGly-Ala-Ser-Chg-Gln-Ser-Leu-Dox (3) | Aminoglycoside (reference prodrug) | 9.8 | 22 |
| GABA←mGly-Ala-Ser-Chg-Gln-NH—O—CH$_2$—C(Me)$_2$C(O)-14-O-Dox (4) | C-14 α-hydroxyl (test prodrug) | 53 | 67 |

2. Biological Assays and Metabolism Studies

A. Cell Culture

Monolayer cultures of PSA-secreting LNCaP and non-PSA-secreting DU145 human prostate carcinoma cells were conducted in growth medium in a $CO_2$ incubator under a humidified atmosphere at 37° C. for 3 weeks prior to initiating cytotoxicity experiments. During cell growth, media were changed every 3 days and trypsinization carried out at 80% confluence with a 1:4 split for subsequent cultures. Cells were grown on 96-well plates for 48 h at initial concentrations of 5000 cells/well. At the end of the 48-h period, the growth medium was replaced by serum-free medium RPMI 1640 medium containing L-glutamine (2 mM), 2% TCM, penicillin G (100 units/mL) and streptomycin sulfate (100 units/mL), and prodrugs added to wells at concentrations ranging from 0.07 to 100 μM. The plates were incubated at 37° C. for 72 h under a humidified $CO_2$ atmosphere, and cell viability determined using the MTT assay. Briefly, 10 μL aliquots of a 12 mM MTT solution were added to wells and the plates incubated in a $CO_2$ incubator under a humidified atmosphere at 37° C. for 4 h. Well contents were then solubilized with 1% SDS (100 μL/well) for 12 h, and $OD_{570}$ values measured on a Dynatech MR5000 plate reader. Cell viability was computed as a percentage of control growth, and $IC_{50}$ values determined as the concentration at which cell growth is inhibited by 50%.

B. Prodrug Cytotoxicity in DU145 and LNCaP Cell Lines

To assess cytotoxicity and tumor selectivity, all prodrugs were incubated in cultured cell lines secreting (LNCaP) or lacking (DU145) PSA for a period of 72 h. Doxorubicin was used as a positive control and cell viability determined at the end of the incubation period using an MTT assay. It was anticipated that peptide prodrugs would be activated extracellularly in LNCaP, but not DU145 cells, by the proteolytic action of PSA releasing doxorubicin that would ultimately lead to cell death. Conjugate 3 was the most cytotoxic prodrug against PSA-secreting LNCaP cells with excellent selectivity against non-PSA-producing DU145 cells (FIG. 8, Table 3). Since PSA cleavage rates among most doxorubicin conjugates 1-3 were similar (FIG. 8, Table 3) alternate unknown mechanisms must have contributed to differences in prodrug selectivity in LNCaP and DU145 tumor cell lines. Despite its lower PSA cleavage rate compared to doxorubicin conjugates 1-3, prodrug 4 exhibited a cytotoxicity profile comparable to that of L-377,202 (prodrug 1). This is attributable to the fact that the cytotoxin released by prodrug 4 is free doxorubicin rather than Leu-doxorubicin for prodrugs 1-3. Because doxorubicin was shown to be 10 times more potent than Leu-Doxorubicin at killing tumor cells, its slower release from prodrug 4 was as effective as the relatively faster release of Leu-Doxorubicin from prodrug 1 (FIG. 9). Moreover, unlike prodrug 1, prodrug 4 does not rely on the hydrolytic action of additional aminopeptidases to generate the final cytotoxin as suggested by LC-MS with accurate mass data analysis (FIG. 10).

TABLE 2

Prodrug Cytotoxicity in PSA-producing LNCaP Cell Lines

| Prodrug | PSA peptide linkage site | LNCaP IC50 (μM) | Selectivity against DU145 |
|---|---|---|---|
| Dox | | <0.07 | 1 |
| Glutaryl-Hyp-Ala-Ser-Chg-Gln-Ser-Leu-Dox (SEQ ID NO: 4) (1) | Aminoglycoside (reference prodrug) | 0.18 | 560 |

TABLE 2-continued

Prodrug Cytotoxicity in PSA-producing LNCaP Cell Lines

| Prodrug | PSA peptide linkage site | LNCaP IC50 (μM) | Selectivity against DU145 |
|---|---|---|---|
| Glutaryl-Ser-Ala-Ser-Chg-Gln-Ser-Leu-Dox (SEQ ID NO: 1) (2) | Aminoglycoside (reference prodrug) | 0.27 | 370 |
| GABA←mGly-Ala-Ser-Chg-Gln-Ser-Leu-Dox (3) | Aminoglycoside (reference prodrug) | 0.082 | 1220 |
| GABA←mGly-Ala-Ser-Chg-Gln-NH—O—CH2—C(Me)2C(O)—14-O-Dox (4) | C-14 α-hydroxyl (test prodrug) | 0.19 | 560 |

The foregoing examples and description of the preferred embodiments should be taken as illustrating, rather than as limiting the present invention as defined by the claims. As will be readily appreciated, numerous variations and combinations of the features set forth above can be utilized without departing from the present disclosure as set forth in the claims. Such variations are not regarded as a departure from the scope of the disclosure, and all such variations are intended to be included within the scope of the following claims. All references cited herein are incorporated by reference in their entireties.

Publications disclosed herein are provided solely for their disclosure prior to the filing date of the present invention. Further, the dates of publication provided may be different from the actual publication dates which may need to be independently confirmed.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

SEQUENCE LISTING

```
<160> NUMBER OF SEQ ID NOS: 9

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Glutaryl on N-terminal end
<220> FEATURE:
<221> NAME/KEY: misc_feature
<222> LOCATION: (4)..(4)
<223> OTHER INFORMATION: Xaa is Chg (cyclohexylglycine)
<220> FEATURE:
<221> NAME/KEY: misc_feature
<222> LOCATION: (7)..(7)
<223> OTHER INFORMATION: Dox on C-terminal end

<400> SEQUENCE: 1

Ser Ala Ser Xaa Gln Ser Leu
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Fm glutaryl on N-terminal end
<220> FEATURE:
<221> NAME/KEY: misc_feature
<222> LOCATION: (4)..(4)
<223> OTHER INFORMATION: Xaa is Chg (cyclohexylglycine)
<220> FEATURE:
```

```
<221> NAME/KEY: misc_feature
<222> LOCATION: (7)..(7)
<223> OTHER INFORMATION: OH on C-terminal end

<400> SEQUENCE: 2

Ser Ala Ser Xaa Gln Ser Leu
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: H on N-terminal end
<220> FEATURE:
<221> NAME/KEY: misc_feature
<222> LOCATION: (3)..(3)
<223> OTHER INFORMATION: Xaa is Chg (cyclohexylglycine)
<220> FEATURE:
<221> NAME/KEY: misc_feature
<222> LOCATION: (6)..(6)
<223> OTHER INFORMATION: OH on C-terminal end

<400> SEQUENCE: 3

Ala Ser Xaa Gln Ser Leu
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Glutaryl Hyp on N-terminal end
<220> FEATURE:
<221> NAME/KEY: misc_feature
<222> LOCATION: (3)..(3)
<223> OTHER INFORMATION: Xaa is Chg (cyclohexylglycine)
<220> FEATURE:
<221> NAME/KEY: misc_feature
<222> LOCATION: (6)..(6)
<223> OTHER INFORMATION: Dox on C-terminal end

<400> SEQUENCE: 4

Ala Ser Xaa Gln Ser Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is GABA, Glutaryl or Y (an N-capping group)
<220> FEATURE:
<221> NAME/KEY: misc_feature
<222> LOCATION: (2)..(2)
<223> OTHER INFORMATION: Xaa is D-mGly, Ser,Dser,- Psi-[NH-CO-NH] or any
      amino acid
<220> FEATURE:
<221> NAME/KEY: misc_feature
<222> LOCATION: (5)..(5)
<223> OTHER INFORMATION: Xaa is Chg (cyclohexylglycine)
```

```
<220> FEATURE:
<221> NAME/KEY: misc_feature
<222> LOCATION: (6)..(6)
<223> OTHER INFORMATION: -NH-U-V-W(Me)2C(O)-O-C on carboxyl end; where
      NH is an amine group; U, if present, is Ser, or is i-Ser; V, if
      present, is O, provided that at least one of U and V is present; W
      is CH2 or NH

<400> SEQUENCE: 5

Xaa Xaa Ala Ser Xaa Gln
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is GABA, Glutaryl or Y (an N-capping group)
<220> FEATURE:
<221> NAME/KEY: misc_feature
<222> LOCATION: (2)..(2)
<223> OTHER INFORMATION: Xaa is D-mGly, Ser,Dser,- Psi-[NH-CO-NH] or any
      amino acid
<220> FEATURE:
<221> NAME/KEY: misc_feature
<222> LOCATION: (5)..(5)
<223> OTHER INFORMATION: Xaa is Chg (cyclohexylglycine)
<220> FEATURE:
<221> NAME/KEY: misc_feature
<222> LOCATION: (6)..(6)
<223> OTHER INFORMATION: -NH-U-V-W(Me)2C(O) on carboxyl end; where NH is
      an amine group; U, if present, is Ser, or is i-Ser; V, if present,
      is O, provided that at least one of U and V is present; W is CH2
      or NH

<400> SEQUENCE: 6

Xaa Xaa Ala Ser Xaa Gln
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is Chg (cyclohexylglycine)

<400> SEQUENCE: 7

Ala Ser Xaa Gln Ser
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is GABA, Glutaryl or Y (an N-capping group)
<220> FEATURE:
<221> NAME/KEY: misc_feature
<222> LOCATION: (2)..(2)
<223> OTHER INFORMATION: Xaa is D-mGly, Ser,Dser,- Psi-[NH-CO-NH] or any
      amino acid
```

```
<220> FEATURE:
<221> NAME/KEY: misc_feature
<222> LOCATION: (5)..(5)
<223> OTHER INFORMATION: Xaa is Chg (cyclohexylglycine)
<220> FEATURE:
<221> NAME/KEY: misc_feature
<222> LOCATION: (6)..(6)
<223> OTHER INFORMATION: -NH-V-W(Me)2C(O)-O-C on carboxyl end; where NH
      is an amine group; U, if present, is Ser, or is i-Ser; V, if
      present, is O, provided that at least one of U and V is present; W
      is CH2 or NH

<400> SEQUENCE: 8

Xaa Xaa Ala Ser Xaa Gln
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is GABA, Glutaryl or Y (an N-capping group)
<220> FEATURE:
<221> NAME/KEY: misc_feature
<222> LOCATION: (2)..(2)
<223> OTHER INFORMATION: Xaa is D-mGly, Ser,Dser,- Psi-[NH-CO-NH] or any
      amino acid
<220> FEATURE:
<221> NAME/KEY: misc_feature
<222> LOCATION: (5)..(5)
<223> OTHER INFORMATION: Xaa is Chg (cyclohexylglycine)
<220> FEATURE:
<221> NAME/KEY: misc_feature
<222> LOCATION: (6)..(6)
<223> OTHER INFORMATION: -NH-U-W(Me)2C(O)-O-C on carboxyl end; where NH
      is an amine group; U, if present, is Ser, or is i-Ser; W is CH2 or
      NH

<400> SEQUENCE: 9

Xaa Xaa Ala Ser Xaa Gln
1               5
```

What is claimed is:

1. An ester prodrug according to Formula I:

```
Formula I
                                          (SEQ ID NO: 5)
A-B-Ala-Ser-Chg-Gln-NH-U-V-W-C(Me)2C(O)—O—C
``` wherein:
A is GABA, Glutaryl or Y;
Y is an N-capping group;
B is ←mGly, Ser, ←DSer-ψ[NH—CO—NH] or X;
X is any amino acid residue;
U is absent;
V is O;
W is $CH_2$;
Chg is cyclohexylglycine; and
C is a chemotherapeutic agent or prostate disease drug.

2. The ester prodrug of claim 1, wherein A is GABA, and B is ←mGly.

3. The ester prodrug of claim 1, wherein A is Glutaryl and B is Ser.

4. The ester prodrug of claim 1, wherein A is GABA and B is ←DSer-ψ[NH—CO—NH].

5. The ester prodrug according to claim 1, wherein the chemotherapeutic or prostate disease agent has a free hydroxyl or hydroxyketone functional group.

6. The ester prodrug according to claim 5, wherein the free hydroxyketone is the hydroxyketone of anthracycline or its analogs.

7. The ester prodrug according to claim 5, wherein the free hydroxyl is the hydroxyketone (C-14 α-hydroxyl) of Doxorubicin or its analogs.

8. The ester prodrug according to claim 5, wherein the chemotherapeutic agent is selected from the group consisting of paclitaxel, thapsigargin, vinblastine, doxorubicin, anthracycline, epirubicin, pirarubicin, and N-acetylated anthracycline analogs.

9. The ester prodrug according to claim 1, wherein the prostate disease agent is selected from the group consisting of silodosin, minoxidil, minoxidil sulfate, prazosin, and doxycycline.

10. The ester prodrug according to claim 1 that is selected from the group consisting of:

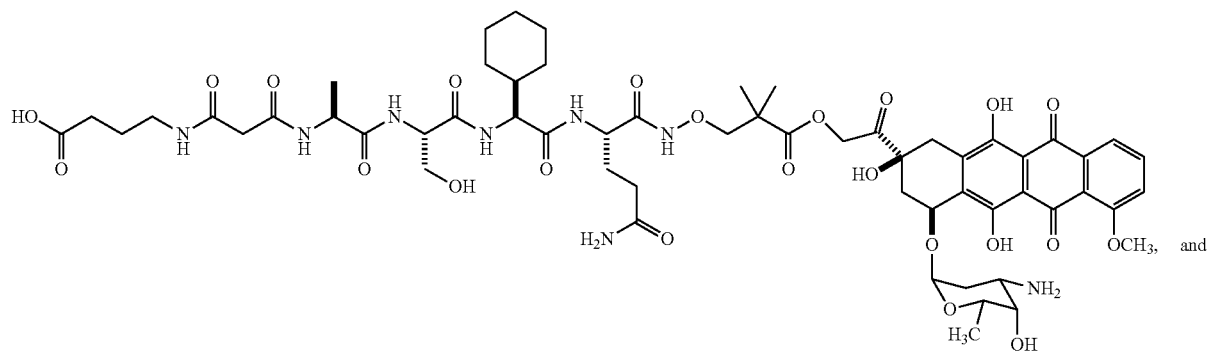

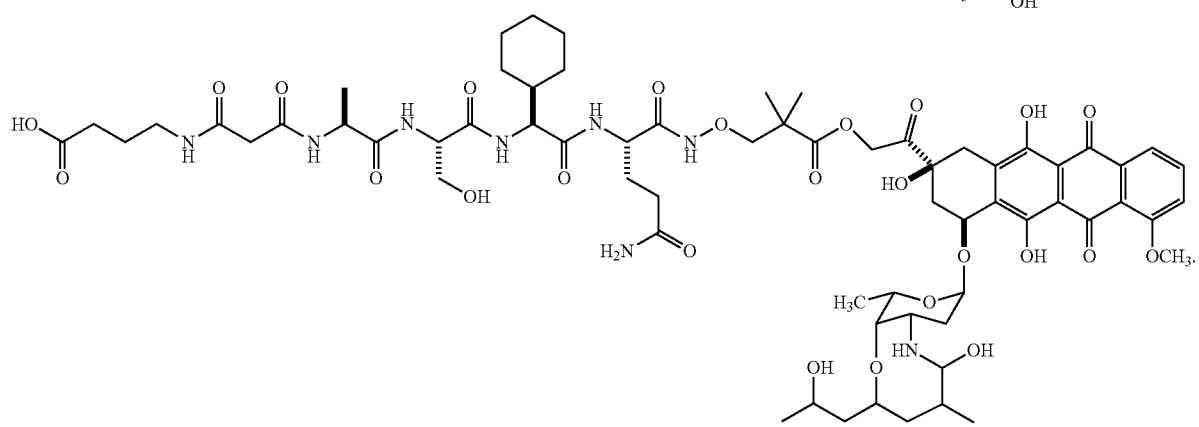

11. A pharmaceutical composition comprising at least one ester prodrug according to claim 1, further comprising a pharmaceutically acceptable carrier, diluent, and/or preservative.

12. A method of treating prostate disease comprising administering to a patient in need thereof an effective amount of at least one prodrug according to claim 1.

13. The method of claim 12, wherein the prostate disease is prostate cancer, prostatis, or BPH.

14. The method of claim 13, wherein the prostate disease is prostate cancer.

15. A PSA-cleavable peptide according to Formula IV

Formula IV
(SEQ ID NO: 6)
A-B-Ala-Ser-Chg-Gln-NH-U-V-W-C(Me)$_2$C(O)— wherein:
A is GABA, Glutaryl or Y;
Y is an N-capping group;
B is ←mGly, Ser, ←DSer-ψ[NH—CO—NH]— or X;
X is any amino acid residue;
U is absent;
V is O;
W is CH$_2$; and
Chg is cyclohexylglycine.

16. The ester prodrug according to claim 1 selected from the group consisting of compounds 4, 7, 11, 14, 17, and 20.

17. The PSA-cleavable peptide according to claim 15 selected from the group consisting of compounds 4, 7, 11, 14, 17, and 20.

18. The ester prodrug according to claim 8, wherein the N-acetylated anthracycline analog is TAN-1120.

* * * * *